United States Patent [19]
Fahl et al.

[11] Patent Number: 6,136,605
[45] Date of Patent: *Oct. 24, 2000

[54] GLUTATHIONE S-TRANSFERASE ISOFORMS

[75] Inventors: William E. Fahl; Andrew M. Gulick; T. Herbert Manoharan, all of Madison, Wis.; Ralph B. Puchalski, La Jolla, Calif.; Katharine Kramer; Wyeth W. Wasserman, both of Madison, Wis.

[73] Assignee: Wisconsin Alumni Research Foundation, Madison, Wis.

[ * ] Notice: This patent is subject to a terminal disclaimer.

[21] Appl. No.: 08/297,431

[22] Filed: Aug. 26, 1994

[51] Int. Cl.$^7$ .......................... C12N 15/00; C12N 15/12; C07H 21/04
[52] U.S. Cl. ..................... 435/440; 536/23.5; 536/24.1
[58] Field of Search ............................... 424/93.2, 93.21; 435/69.1, 172.1, 320.1, 440; 536/23.1, 23.5, 24.1

[56] References Cited

PUBLICATIONS

Batist, G., et al., "Overexpression of a Novel Anionic Glutathione Transferase in Multidrug–resistant Human Breast Cancer Cells," *Journal of Biological Chemistry* 261:15544–15549(1986).

Deisseroth, A. B., "Current Trends and Future Directions in the Genetic Therapy of Human Neoplastic Disease," *Cancer* 72:2069–2074(1993).

Dolan, M.E., et al., "Comparison of the inactivation of mammalian and bacterial $O^6$–alkylguanine–DNA alkyltransferases by $O^6$–benzylguanine and $O^6$–methylguanine," *Carcinogenesis* 12:2305–2309 (1991).

Fahl, W. E., et al., "Mechanisms Through Which Glutathione S–Transferase–Mediated Resistance to Alkylating Molecules Can Be Augmented," *Structure and Function of Glutathione Transferases*, edited by K. D. Tew et al., CRC Press, Boca Raton, 1993.

Hancock, J. F., et al., "All *ras* Proteins Are Polyisoprenylated but Only Some Are Palmitoylated," *Cell* 57:1167–1177(1989).

Hancock, J.F., et al., "A Polybasic Domain or Palmitoylation is Required in Addition to the CAAX Motif to Localize $p21^{ras}$ to the Plasma Membrane," *Cell* 63:133–139 (1990).

Ji, X., et al., "Snapshots along the Reaction Coordinate of an $S_NAr$ Reaction Catalyzed by Glutathione Transferase," *Biochemistry* 32: 12949–12954(1993).

Ji, X., et al., "Structure and Function of the Xenobiotic Substrate Binding Site of a Glutathione S–Transferase As Revealed by X–ray Crystallographic Analysis of Product Complexes with the Diastereomers of 9–(S–glutathionyl)–10–hydroxy–9,10–dihydrophenanthrene," *Biochemistry* 33:1043–1052 (1994).

Manoharan, T. H., et al., "Expression of Tandem Glutathione S–Transferase Recombinant Genes in COS Cells for Analysis of Efficiency of Protein Expression and Associated Drug Resistance," *Molecular Pharmacology* 39:461–467 (1991).

Manoharan, T. H., et al., "Structural Studies on Human Glutathione S–Transferase π," *Journal of Biological Chemistry* 267:18940–18945(1992).

Picard, D., and K.R. Yamamoto, "Two signals mediate hormone–dependent nuclear localization of the glucocorticoid receptor," *The EMBO Journal* 6:3333–3340 (1987).

*Primary Examiner*—Robert A. Schwartzman
*Attorney, Agent, or Firm*—Janet E. Reed; Saul Ewing Remick & Saul, LLP

[57] ABSTRACT

A method is described for the creation of novel isoforms of the enzyme glutathione S-transferase which have enhanced activity in host cells against specific toxic agents. The method includes site directed mutagenesis and selection with the targeted agent in the host cells. The sites of directed mutagenesis is the site of electrophile binding by the native form of the enzyme. This site has proven susceptible to manipulation without loss of enzymatic activity. Various techniques for enhancing the expression, activity, or localization of the expressed enzyme in mammalian cells are described. Genes for the mutant isoforms of the enzyme may be useful in cancer therapeutics to confer upon selected groups of cells heightened resistance to antineoplastic agents.

11 Claims, 5 Drawing Sheets

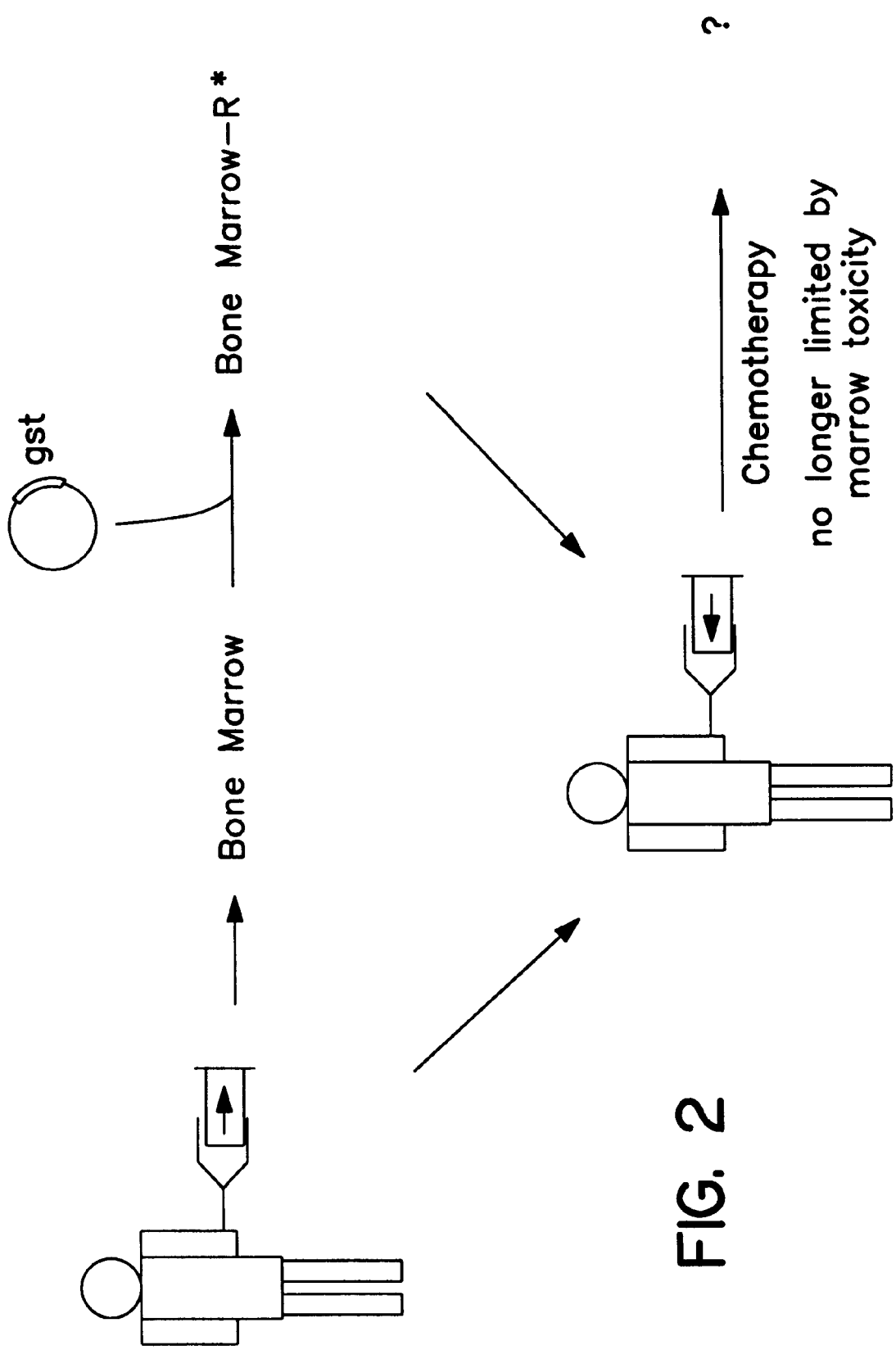

```
                 1                                                                           72
Rat GST 2-2      PGKPVLHYF DGRGRMEPIR WLLAAAGVEF EEQFLKT... ....RDDLAR LRNDGSLMFQ QVPMVEIDGM KLVQTRAILN
Hum GST A1-1     AEKPKLHYF NARGRMESTR WLLAAAGVEF EEKFIKS... ....AEDLDK LRNDGYLMFQ QVPMVEIDGM KLVQTRAILN
Rat GST 3-3      PMILGYW NVRGLTHPIR LLLEYTDSSY EEKRYAMGDA PDYDRSQWLN EKFKLGLDFP NLPYLIDGSR KITQSNAIMR
Hum GST P1-1     APYTVVYF PVRGRCAALR MLLADQGQSW ......KEEVVTV ......ETWQE GSLKASCLYG QLPKFQDGDL TLYQSNTILR 73                                                                          150
Rat GST 2-2      YIATKYNLYG KDMKERALID MYAEGVADLD EIVLHYPYIP PGEKEASLAK IKDKARNRYF PAFEKVLKSH G..QDYLVGN
Hum GST A1-1     YIASKYNLYG KDIKERALID MYIEGIADLG EMILLLPVCP PEEKDAKLAL IKEKIKNRYF PAFEKVLKSH G..QDYLVGN
Rat GST 3-3      YLARKHHLCG ETEEERIRAD IVENQVMDNR MQLIMLCYNP D..FEKQKPE FLKTIPE.KM KLYSEFLG.. K..RPWFAGD
Hum GST P1-1     HLGRTLGLYG KDQQEAALVD MVNDGVEDLR CKYISLIYTN ...YEAGKDD YVKALPG.QL KPFETLLSQN QGGKTFIVGD 151                                                                         220
Rat GST 2-2      RLSRADVYLV QVLYHVEELD PSALANFPLL KALRTRVSNL PTVKKFLQPG SQRKPLEDEK CVESAVKIFS *
Hum GST A1-1     KLSRADIHLV ELLYYVEELD SSLISSFPLL KALKTRISNL PTVKKFLQPG SPRKPPMDEK SLEEARKIFR F*
Rat GST 3-3      KVTYVDFLAY DILDQYHIFE PKCLDAFPNL KDFLARFEGL KKISAYMNCS RYLSTPIFSK LAQWSNK*
Hum GST P1-1     QISFADYNLL DLLIHEVLA PGCLDAFPLL SAYVGRLSAR PKLKAFLASP EYVNLPINGN GKQ*
```

FIG. 3

```
1                                              45.ATG CG
51   GGG AAG CCA G TC CTT CAC TA C TTC GAT GGC  AGG GGG AGA A T GAG CCC AT
                    A              GCGAAGATC    9-11s1
                    A              GTGTGCATC    9-11s4
                    A              ATGAAGATC    9-11s7
                    A              GTGCGCATC    9-11s9
                    A              GGGATCTTG    9-11s15
                    A              GTCCCCTC     9-11s16
                    A              GTGATCTGC    9-11s21
                    A              TGCGACATC    9-11s22
                    A              TTAGATGGC    WCs3

101  CCGGTGGCTC CTGGCTGCAG CTGGAGTAGA GTTTGAAGAA CAATTTCTGA

151  AAACTCGGGA TGACCTGGCC AGGCTAAGGA ATGATGGGAG TTTGATGTTC

201  CAGCAAGTGC CCATGGTGGA GATTGATGGG ATGAAGCTGG TGCAGACCAG

251  AGCCATTCTC AACTACATTG CCACCAAATA CAACCTCTAT GGGAAGGACA

301  TGAAGGAGAG AGCCCTCATC GACATGTATG CAGAAGGAGT GGCGGATCTG

351  GATGAAATAG TTCTCCATTA CCCTTACATT CCCCCTGGGG AGAAAGAGGC

401  AAGTCTTGCC AAAATCAAGG ACAAAGCAAG GAACCGTTAC TTTCCTGCCT

451  TTGAAAAGGT GTTGAAGAGC CATGGACAAG ATTATCTCGT TGGCAATAGG

501  CTGAGCAGAG CTGATGTTTA CCTAGTTCAA GTTCTCTACC ATGTGGAAGA

551  GCTGGACCCC AGCGCTTTGG CCAACTTCCC TCTGCTGAAG GCCCTGAGAA

601  CCAGAGTCAG CAACCTCCCC ACAGTGAAGA AGTTTCTTCA GCCTGGCAGC

651  CAGAGGAAGC CATTAGAGGA TGAGAAATGT GTAGAATCTG CAGTTAAGAT

701  CTTCAGTTAA
```

FIG. 5

SEQUENCE LISTING (1) GENERAL INFORMATION:

(iii) NUMBER OF SEQUENCES: 34

(2) INFORMATION FOR SEQ ID NO:1:

(i) SEQUENCE CHARACTERISTICS:
      (A) LENGTH: 959 base pairs
      (B) TYPE: nucleic acid
      (C) STRANDEDNESS: double
      (D) TOPOLOGY: linear (ii) MOLECULE TYPE: DNA (genomic)

(ix) FEATURE:
      (A) NAME/KEY: CDS
      (B) LOCATION: 45..710

(xi) SEQUENCE DESCRIPTION: SEQ ID NO:1:

```
AGAGGGAGCA GCTTTTTAAC AAGAGAACTC AAGCAATTGC TGCC ATG CCG GGG AAG        56
                                                Met Pro Gly Lys
                                                  1

CCA GTC CTT CAC TAC TTC GAT GGC AGG GGG AGA ATG GAG CCC ATC CGG       104
Pro Val Leu His Tyr Phe Asp Gly Arg Gly Arg Met Glu Pro Ile Arg
  5              10                  15                  20

TGG CTC CTG GCT GCA GCT GGA GTA GAG TTT GAA GAA CAA TTT CTG AAA       152
Trp Leu Leu Ala Ala Ala Gly Val Glu Phe Glu Glu Gln Phe Leu Lys
                 25                  30                  35

ACT CGG GAT GAC CTG GCC AGG CTA AGG AAT GAT GGG AGT TTG ATG TTC       200
Thr Arg Asp Asp Leu Ala Arg Leu Arg Asn Asp Gly Ser Leu Met Phe
             40                  45                  50

CAG CAA GTG CCC ATG GTG GAG ATT GAT GGG ATG AAG CTG GTG CAG ACC       248
Gln Gln Val Pro Met Val Glu Ile Asp Gly Met Lys Leu Val Gln Thr
             55                  60                  65

AGA GCC ATT CTC AAC TAC ATT GCC ACC AAA TAC AAC CTC TAT GGG AAG       296
Arg Ala Ile Leu Asn Tyr Ile Ala Thr Lys Tyr Asn Leu Tyr Gly Lys
 70                  75                  80

GAC ATG AAG GAG AGA GCC CTC ATC GAC ATG TAT GCA GAA GGA GTG GCG       344
Asp Met Lys Glu Arg Ala Leu Ile Asp Met Tyr Ala Glu Gly Val Ala
 85                  90                  95                 100

GAT CTG GAT GAA ATA GTT CTC CAT TAC CCT TAC ATT CCC CCT GGG GAG       392
Asp Leu Asp Glu Ile Val Leu His Tyr Pro Tyr Ile Pro Pro Gly Glu
                105                 110                 115

AAA GAG GCA AGT CTT GCC AAA ATC AAG GAC AAA GCA AGG AAC CGT TAC       440
Lys Glu Ala Ser Leu Ala Lys Ile Lys Asp Lys Ala Arg Asn Arg Tyr
            120                 125                 130

TTT CCT GCC TTT GAA AAG GTG TTG AAG AGC CAT GGA CAA GAT TAT CTC       488
Phe Pro Ala Phe Glu Lys Val Leu Lys Ser His Gly Gln Asp Tyr Leu
```

-continued

```
            135                 140                 145
GTT GGC AAT AGG CTG AGC AGA GCT GAT GTT TAC CTA GTT CAA GTT CTC       536
Val Gly Asn Arg Leu Ser Arg Ala Asp Val Tyr Leu Val Gln Val Leu
        150                 155                 160

TAC CAT GTG GAA GAG CTG GAC CCC AGC GCT TTG GCC AAC TTC CCT CTG       584
Tyr His Val Glu Glu Leu Asp Pro Ser Ala Leu Ala Asn Phe Pro Leu
165                 170                 175                 180

CTG AAG GCC CTG AGA ACC AGA GTC AGC AAC CTC CCC ACA GTG AAG AAG       632
Leu Lys Ala Leu Arg Thr Arg Val Ser Asn Leu Pro Thr Val Lys Lys
                185                 190                 195

TTT CTT CAG CCT GGC AGC CAG AGG AAG CCA TTA GAG GAT GAG AAA TGT       680
Phe Leu Gln Pro Gly Ser Gln Arg Lys Pro Leu Glu Asp Glu Lys Cys
            200                 205                 210

GTA GAA TCT GCA GTT AAG ATC TTC AGT TAATTCAGGC ATCTATGGAT             727
Val Glu Ser Ala Val Lys Ile Phe Ser
        215                 220

ACACTGTACC CACAAAGCCA GCCTTCGAAA GCTTTGCAAC AATCGCATAT TTTGACTAAA     787

TGTTGACCCT ACTTATTGGG AGGCCAACAC GTTTTCTAAT GCTTCTGTGT TAATTCATAT     847

AGACATGACT GATGAGGAAT TGCTGGGATG CTATTTGGTT GTAGTTAAAA TTTGAAATCA     907

TGATCACTTC CTCAGATATT ACTTTGAATC TCAATAAAAA CTTCGCAAGC TT            959
```

(2) INFORMATION FOR SEQ ID NO:2:

(i) SEQUENCE CHARACTERISTICS:
        (A) LENGTH: 221 amino acids
        (B) TYPE: amino acid
        (D) TOPOLOGY: linear (ii) MOLECULE TYPE: protein (xi) SEQUENCE DESCRIPTION: SEQ ID NO:2:

```
Met Pro Gly Lys Pro Val Leu His Tyr Phe Asp Gly Arg Gly Arg Met
 1               5                  10                  15

Glu Pro Ile Arg Trp Leu Leu Ala Ala Ala Gly Val Glu Phe Glu Glu
             20                  25                  30

Gln Phe Leu Lys Thr Arg Asp Asp Leu Ala Arg Leu Arg Asn Asp Gly
         35                  40                  45

Ser Leu Met Phe Gln Gln Val Pro Met Val Glu Ile Asp Gly Met Lys
     50                  55                  60

Leu Val Gln Thr Arg Ala Ile Leu Asn Tyr Ile Ala Thr Lys Tyr Asn
 65                  70                  75                  80

Leu Tyr Gly Lys Asp Met Lys Glu Arg Ala Leu Ile Asp Met Tyr Ala
                 85                  90                  95

Glu Gly Val Ala Asp Leu Asp Glu Ile Val Leu His Tyr Pro Tyr Ile
             100                 105                 110

Pro Pro Gly Glu Lys Glu Ala Ser Leu Ala Lys Ile Lys Asp Lys Ala
         115                 120                 125

Arg Asn Arg Tyr Phe Pro Ala Phe Glu Lys Val Leu Lys Ser His Gly
     130                 135                 140

Gln Asp Tyr Leu Val Gly Asn Arg Leu Ser Arg Ala Asp Val Tyr Leu
145                 150                 155                 160

Val Gln Val Leu Tyr His Val Glu Glu Leu Asp Pro Ser Ala Leu Ala
                 165                 170                 175

Asn Phe Pro Leu Leu Lys Ala Leu Arg Thr Arg Val Ser Asn Leu Pro
             180                 185                 190

Thr Val Lys Lys Phe Leu Gln Pro Gly Ser Gln Arg Lys Pro Leu Glu
```

```
                195                 200                 205
Asp Glu Lys Cys Val Glu Ser Ala Val Lys Ile Phe Ser
    210                 215                 220

(2) INFORMATION FOR SEQ ID NO:3:

(i) SEQUENCE CHARACTERISTICS:
        (A) LENGTH: 959 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (B) STRAIN: 9-11s1

(ix) FEATURE:
        (A) NAME/KEY: CDS
        (B) LOCATION: 45..710

(xi) SEQUENCE DESCRIPTION: SEQ ID NO:3:

AGAGGGAGCA GCTTTTTAAC AAGAGAACTC AAGCAATTGC TGCC ATG CCG GGG AAG        56
                                                  Met Pro Gly Lys
                                                   1

CCA GTA CTT CAC TAC GCG AAG ATC AGG GGG AGA ATG GAG CCC ATC CGG       104
Pro Val Leu His Tyr Ala Lys Ile Arg Gly Arg Met Glu Pro Ile Arg
  5              10                  15                  20

TGG CTC CTG GCT GCA GCT GGA GTA GAG TTT GAA GAA CAA TTT CTG AAA       152
Trp Leu Leu Ala Ala Ala Gly Val Glu Phe Glu Glu Gln Phe Leu Lys
                25                  30                  35

ACT CGG GAT GAC CTG GCC AGG CTA AGG AAT GAT GGG AGT TTG ATG TTC       200
Thr Arg Asp Asp Leu Ala Arg Leu Arg Asn Asp Gly Ser Leu Met Phe
             40                  45                  50

CAG CAA GTG CCC ATG GTG GAG ATT GAT GGG ATG AAG CTG GTG CAG ACC       248
Gln Gln Val Pro Met Val Glu Ile Asp Gly Met Lys Leu Val Gln Thr
         55                  60                  65

AGA GCC ATT CTC AAC TAC ATT GCC ACC AAA TAC AAC CTC TAT GGG AAG       296
Arg Ala Ile Leu Asn Tyr Ile Ala Thr Lys Tyr Asn Leu Tyr Gly Lys
     70                  75                  80

GAC ATG AAG GAG AGA GCC CTC ATC GAC ATG TAT GCA GAA GGA GTG GCG       344
Asp Met Lys Glu Arg Ala Leu Ile Asp Met Tyr Ala Glu Gly Val Ala
 85                  90                  95                 100

GAT CTG GAT GAA ATA GTT CTC CAT TAC CCT TAC ATT CCC CCT GGG GAG       392
Asp Leu Asp Glu Ile Val Leu His Tyr Pro Tyr Ile Pro Pro Gly Glu
                105                 110                 115

AAA GAG GCA AGT CTT GCC AAA ATC AAG GAC AAA GCA AGG AAC CGT TAC       440
Lys Glu Ala Ser Leu Ala Lys Ile Lys Asp Lys Ala Arg Asn Arg Tyr
            120                 125                 130

TTT CCT GCC TTT GAA AAG GTG TTG AAG AGC CAT GGA CAA GAT TAT CTC       488
Phe Pro Ala Phe Glu Lys Val Leu Lys Ser His Gly Gln Asp Tyr Leu
        135                 140                 145

GTT GGC AAT AGG CTG AGC AGA GCT GAT GTT TAC CTA GTT CAA GTT CTC       536
Val Gly Asn Arg Leu Ser Arg Ala Asp Val Tyr Leu Val Gln Val Leu
    150                 155                 160

TAC CAT GTG GAA GAG CTG GAC CCC AGC GCT TTG GCC AAC TTC CCT CTG       584
Tyr His Val Glu Glu Leu Asp Pro Ser Ala Leu Ala Asn Phe Pro Leu
165                 170                 175                 180

CTG AAG GCC CTG AGA ACC AGA GTC AGC AAC CTC CCC ACA GTG AAG AAG       632
Leu Lys Ala Leu Arg Thr Arg Val Ser Asn Leu Pro Thr Val Lys Lys
                185                 190                 195

TTT CTT CAG CCT GGC AGC CAG AGG AAG CCA TTA GAG GAT GAG AAA TGT       680
Phe Leu Gln Pro Gly Ser Gln Arg Lys Pro Leu Glu Asp Glu Lys Cys
```

```
                200                 205                 210
GTA GAA TCT GCA GTT AAG ATC TTC AGT TAATTCAGGC ATCTATGGAT          727
Val Glu Ser Ala Val Lys Ile Phe Ser
            215                 220

ACACTGTACC CACAAAGCCA GCCTTCGAAA GCTTTGCAAC AATCGCATAT TTTGACTAAA   787

TGTTGACCCT ACTTATTGGG AGGCCAACAC GTTTTCTAAT GCTTCTGTGT TAATTCATAT   847

AGACATGACT GATGAGGAAT TGCTGGGATG CTATTTGGTT GTAGTTAAAA TTTGAAATCA   907

TGATCACTTC CTCAGATATT ACTTTGAATC TCAATAAAAA CTTCGCAAGC TT          959
```

(2) INFORMATION FOR SEQ ID NO:4:

(i) SEQUENCE CHARACTERISTICS:
        (A) LENGTH: 221 amino acids
        (B) TYPE: amino acid
        (D) TOPOLOGY: linear (ii) MOLECULE TYPE: protein (xi) SEQUENCE DESCRIPTION: SEQ ID NO:4:

```
Met Pro Gly Lys Pro Val Leu His Tyr Ala Lys Ile Arg Gly Arg Met
 1               5                  10                  15

Glu Pro Ile Arg Trp Leu Leu Ala Ala Ala Gly Val Glu Phe Glu Glu
                20                  25                  30

Gln Phe Leu Lys Thr Arg Asp Asp Leu Ala Arg Leu Arg Asn Asp Gly
            35                  40                  45

Ser Leu Met Phe Gln Gln Val Pro Met Val Glu Ile Asp Gly Met Lys
        50                  55                  60

Leu Val Gln Thr Arg Ala Ile Leu Asn Tyr Ile Ala Thr Lys Tyr Asn
65                  70                  75                  80

Leu Tyr Gly Lys Asp Met Lys Glu Arg Ala Leu Ile Asp Met Tyr Ala
                85                  90                  95

Glu Gly Val Ala Asp Leu Asp Glu Ile Val Leu His Tyr Pro Tyr Ile
                100                 105                 110

Pro Pro Gly Glu Lys Glu Ala Ser Leu Ala Lys Ile Lys Asp Lys Ala
            115                 120                 125

Arg Asn Arg Tyr Phe Pro Ala Phe Glu Lys Val Leu Lys Ser His Gly
        130                 135                 140

Gln Asp Tyr Leu Val Gly Asn Arg Leu Ser Arg Ala Asp Val Tyr Leu
145                 150                 155                 160

Val Gln Val Leu Tyr His Val Glu Glu Leu Asp Pro Ser Ala Leu Ala
                165                 170                 175

Asn Phe Pro Leu Leu Lys Ala Leu Arg Thr Arg Val Ser Asn Leu Pro
                180                 185                 190

Thr Val Lys Lys Phe Leu Gln Pro Gly Ser Gln Arg Lys Pro Leu Glu
            195                 200                 205

Asp Glu Lys Cys Val Glu Ser Ala Val Lys Ile Phe Ser
        210                 215                 220
```

(2) INFORMATION FOR SEQ ID NO:5:

(i) SEQUENCE CHARACTERISTICS:
        (A) LENGTH: 959 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
    (B) STRAIN: 9-11s4

(ix) FEATURE:
    (A) NAME/KEY: CDS
    (B) LOCATION: 45..710

(xi) SEQUENCE DESCRIPTION: SEQ ID NO:5:

```
AGAGGGAGCA GCTTTTTAAC AAGAGAACTC AAGCAATTGC TGCC ATG CCG GGG AAG        56
                                                   Met Pro Gly Lys
                                                     1

CCA GTA CTT CAC TAC GTG TGC ATC AGG GGG AGA ATG GAG CCC ATC CGG       104
Pro Val Leu His Tyr Val Cys Ile Arg Gly Arg Met Glu Pro Ile Arg
  5              10                  15                  20

TGG CTC CTG GCT GCA GCT GGA GTA GAG TTT GAA GAA CAA TTT CTG AAA       152
Trp Leu Leu Ala Ala Ala Gly Val Glu Phe Glu Glu Gln Phe Leu Lys
                 25                  30                  35

ACT CGG GAT GAC CTG GCC AGG CTA AGG AAT GAT GGG AGT TTG ATG TTC       200
Thr Arg Asp Asp Leu Ala Arg Leu Arg Asn Asp Gly Ser Leu Met Phe
             40                  45                  50

CAG CAA GTG CCC ATG GTG GAG ATT GAT GGG ATG AAG CTG GTG CAG ACC       248
Gln Gln Val Pro Met Val Glu Ile Asp Gly Met Lys Leu Val Gln Thr
         55                  60                  65

AGA GCC ATT CTC AAC TAC ATT GCC ACC AAA TAC AAC CTC TAT GGG AAG       296
Arg Ala Ile Leu Asn Tyr Ile Ala Thr Lys Tyr Asn Leu Tyr Gly Lys
     70                  75                  80

GAC ATG AAG GAG AGA GCC CTC ATC GAC ATG TAT GCA GAA GGA GTG GCG       344
Asp Met Lys Glu Arg Ala Leu Ile Asp Met Tyr Ala Glu Gly Val Ala
 85                  90                  95                 100

GAT CTG GAT GAA ATA GTT CTC CAT TAC CCT TAC ATT CCC CCT GGG GAG       392
Asp Leu Asp Glu Ile Val Leu His Tyr Pro Tyr Ile Pro Pro Gly Glu
                105                 110                 115

AAA GAG GCA AGT CTT GCC AAA ATC AAG GAC AAA GCA AGG AAC CGT TAC       440
Lys Glu Ala Ser Leu Ala Lys Ile Lys Asp Lys Ala Arg Asn Arg Tyr
            120                 125                 130

TTT CCT GCC TTT GAA AAG GTG TTG AAG AGC CAT GGA CAA GAT TAT CTC       488
Phe Pro Ala Phe Glu Lys Val Leu Lys Ser His Gly Gln Asp Tyr Leu
        135                 140                 145

GTT GGC AAT AGG CTG AGC AGA GCT GAT GTT TAC CTA GTT CAA GTT CTC       536
Val Gly Asn Arg Leu Ser Arg Ala Asp Val Tyr Leu Val Gln Val Leu
    150                 155                 160

TAC CAT GTG GAA GAG CTG GAC CCC AGC GCT TTG GCC AAC TTC CCT CTG       584
Tyr His Val Glu Glu Leu Asp Pro Ser Ala Leu Ala Asn Phe Pro Leu
165                 170                 175                 180

CTG AAG GCC CTG AGA ACC AGA GTC AGC AAC CTC CCC ACA GTG AAG AAG       632
Leu Lys Ala Leu Arg Thr Arg Val Ser Asn Leu Pro Thr Val Lys Lys
                185                 190                 195

TTT CTT CAG CCT GGC AGC CAG AGG AAG CCA TTA GAG GAT GAG AAA TGT       680
Phe Leu Gln Pro Gly Ser Gln Arg Lys Pro Leu Glu Asp Glu Lys Cys
            200                 205                 210

GTA GAA TCT GCA GTT AAG ATC TTC AGT TAATTCAGGC ATCTATGGAT             727
Val Glu Ser Ala Val Lys Ile Phe Ser
        215                 220

ACACTGTACC CACAAAGCCA GCCTTCGAAA GCTTTGCAAC AATCGCATAT TTTGACTAAA     787

TGTTGACCCT ACTTATTGGG AGGCCAACAC GTTTTCTAAT GCTTCTGTGT TAATTCATAT     847

AGACATGACT GATGAGGAAT TGCTGGGATG CTATTTGGTT GTAGTTAAAA TTTGAAATCA     907

TGATCACTTC CTCAGATATT ACTTTGAATC TCAATAAAAA CTTCGCAAGC TT             959
```

(2) INFORMATION FOR SEQ ID NO:6:

(i) SEQUENCE CHARACTERISTICS:
              (A) LENGTH: 221 amino acids
              (B) TYPE: amino acid
              (D) TOPOLOGY: linear (ii) MOLECULE TYPE: protein (xi) SEQUENCE DESCRIPTION: SEQ ID NO:6:

Met Pro Gly Lys Pro Val Leu His Tyr Val Cys Ile Arg Gly Arg Met
  1               5                  10                  15

Glu Pro Ile Arg Trp Leu Leu Ala Ala Ala Gly Val Glu Phe Glu Glu
             20                  25                  30

Gln Phe Leu Lys Thr Arg Asp Asp Leu Ala Arg Leu Arg Asn Asp Gly
         35                  40                  45

Ser Leu Met Phe Gln Gln Val Pro Met Val Glu Ile Asp Gly Met Lys
 50                  55                  60

Leu Val Gln Thr Arg Ala Ile Leu Asn Tyr Ile Ala Thr Lys Tyr Asn
 65                  70                  75                  80

Leu Tyr Gly Lys Asp Met Lys Glu Arg Ala Leu Ile Asp Met Tyr Ala
             85                  90                  95

Glu Gly Val Ala Asp Leu Asp Glu Ile Val Leu His Tyr Pro Tyr Ile
            100                 105                 110

Pro Pro Gly Glu Lys Glu Ala Ser Leu Ala Lys Ile Lys Asp Lys Ala
        115                 120                 125

Arg Asn Arg Tyr Phe Pro Ala Phe Glu Lys Val Leu Lys Ser His Gly
130                 135                 140

Gln Asp Tyr Leu Val Gly Asn Arg Leu Ser Arg Ala Asp Val Tyr Leu
145                 150                 155                 160

Val Gln Val Leu Tyr His Val Glu Glu Leu Asp Pro Ser Ala Leu Ala
                165                 170                 175

Asn Phe Pro Leu Leu Lys Ala Leu Arg Thr Arg Val Ser Asn Leu Pro
            180                 185                 190

Thr Val Lys Lys Phe Leu Gln Pro Gly Ser Gln Arg Lys Pro Leu Glu
        195                 200                 205

Asp Glu Lys Cys Val Glu Ser Ala Val Lys Ile Phe Ser
210                 215                 220

(2) INFORMATION FOR SEQ ID NO:7:

(i) SEQUENCE CHARACTERISTICS:
              (A) LENGTH: 959 base pairs
              (B) TYPE: nucleic acid
              (C) STRANDEDNESS: double
              (D) TOPOLOGY: linear (ii) MOLECULE TYPE: DNA (genomic)

(vi) ORIGINAL SOURCE:
              (B) STRAIN: 9-11s7

(ix) FEATURE:
              (A) NAME/KEY: CDS
              (B) LOCATION: 45..710

(xi) SEQUENCE DESCRIPTION: SEQ ID NO:7:

AGAGGGAGCA GCTTTTTAAC AAGAGAACTC AAGCAATTGC TGCC ATG CCG GGG AAG      56
                                                Met Pro Gly Lys
                                                  1

CCA GTA CTT CAC TAC ATG AAG ATC AGG GGG AGA ATG GAG CCC ATC CGG    104
Pro Val Leu His Tyr Met Lys Ile Arg Gly Arg Met Glu Pro Ile Arg
  5                  10                  15                  20

```
TGG CTC CTG GCT GCA GCT GGA GTA GAG TTT GAA GAA CAA TTT CTG AAA        152
Trp Leu Leu Ala Ala Ala Gly Val Glu Phe Glu Glu Gln Phe Leu Lys
             25                  30                  35

ACT CGG GAT GAC CTG GCC AGG CTA AGG AAT GAT GGG AGT TTG ATG TTC        200
Thr Arg Asp Asp Leu Ala Arg Leu Arg Asn Asp Gly Ser Leu Met Phe
             40                  45                  50

CAG CAA GTG CCC ATG GTG GAG ATT GAT GGG ATG AAG CTG GTG CAG ACC        248
Gln Gln Val Pro Met Val Glu Ile Asp Gly Met Lys Leu Val Gln Thr
             55                  60                  65

AGA GCC ATT CTC AAC TAC ATT GCC ACC AAA TAC AAC CTC TAT GGG AAG        296
Arg Ala Ile Leu Asn Tyr Ile Ala Thr Lys Tyr Asn Leu Tyr Gly Lys
         70                  75                  80

GAC ATG AAG GAG AGA GCC CTC ATC GAC ATG TAT GCA GAA GGA GTG GCG        344
Asp Met Lys Glu Arg Ala Leu Ile Asp Met Tyr Ala Glu Gly Val Ala
85                  90                  95                 100

GAT CTG GAT GAA ATA GTT CTC CAT TAC CCT TAC ATT CCC CCT GGG GAG        392
Asp Leu Asp Glu Ile Val Leu His Tyr Pro Tyr Ile Pro Pro Gly Glu
                105                 110                 115

AAA GAG GCA AGT CTT GCC AAA ATC AAG GAC AAA GCA AGG AAC CGT TAC        440
Lys Glu Ala Ser Leu Ala Lys Ile Lys Asp Lys Ala Arg Asn Arg Tyr
            120                 125                 130

TTT CCT GCC TTT GAA AAG GTG TTG AAG AGC CAT GGA CAA GAT TAT CTC        488
Phe Pro Ala Phe Glu Lys Val Leu Lys Ser His Gly Gln Asp Tyr Leu
            135                 140                 145

GTT GGC AAT AGG CTG AGC AGA GCT GAT GTT TAC CTA GTT CAA GTT CTC        536
Val Gly Asn Arg Leu Ser Arg Ala Asp Val Tyr Leu Val Gln Val Leu
        150                 155                 160

TAC CAT GTG GAA GAG CTG GAC CCC AGC GCT TTG GCC AAC TTC CCT CTG        584
Tyr His Val Glu Glu Leu Asp Pro Ser Ala Leu Ala Asn Phe Pro Leu
165                 170                 175                 180

CTG AAG GCC CTG AGA ACC AGA GTC AGC AAC CTC CCC ACA GTG AAG AAG        632
Leu Lys Ala Leu Arg Thr Arg Val Ser Asn Leu Pro Thr Val Lys Lys
            185                 190                 195

TTT CTT CAG CCT GGC AGC CAG AGG AAG CCA TTA GAG GAT GAG AAA TGT        680
Phe Leu Gln Pro Gly Ser Gln Arg Lys Pro Leu Glu Asp Glu Lys Cys
            200                 205                 210

GTA GAA TCT GCA GTT AAG ATC TTC AGT TAATTCAGGC ATCTATGGAT             727
Val Glu Ser Ala Val Lys Ile Phe Ser
            215                 220

ACACTGTACC CACAAAGCCA GCCTTCGAAA GCTTTGCAAC AATCGCATAT TTTGACTAAA      787

TGTTGACCCT ACTTATTGGG AGGCCAACAC GTTTTCTAAT GCTTCTGTGT TAATTCATAT      847

AGACATGACT GATGAGGAAT TGCTGGGATG CTATTTGGTT GTAGTTAAAA TTTGAAATCA      907

TGATCACTTC CTCAGATATT ACTTTGAATC TCAATAAAAA CTTCGCAAGC TT             959
```

(2) INFORMATION FOR SEQ ID NO:8:

(i) SEQUENCE CHARACTERISTICS:
        (A) LENGTH: 221 amino acids
        (B) TYPE: amino acid
        (D) TOPOLOGY: linear (ii) MOLECULE TYPE: protein (xi) SEQUENCE DESCRIPTION: SEQ ID NO:8:

```
Met Pro Gly Lys Pro Val Leu His Tyr Met Lys Ile Arg Gly Arg Met
 1               5                  10                  15

Glu Pro Ile Arg Trp Leu Leu Ala Ala Ala Gly Val Glu Phe Glu Glu
            20                  25                  30
```

```
Gln Phe Leu Lys Thr Arg Asp Asp Leu Ala Arg Leu Arg Asn Asp Gly
             35                  40                  45

Ser Leu Met Phe Gln Gln Val Pro Met Val Glu Ile Asp Gly Met Lys
 50                  55                  60

Leu Val Gln Thr Arg Ala Ile Leu Asn Tyr Ile Ala Thr Lys Tyr Asn
 65                  70                  75                  80

Leu Tyr Gly Lys Asp Met Lys Glu Arg Ala Leu Ile Asp Met Tyr Ala
                 85                  90                  95

Glu Gly Val Ala Asp Leu Asp Glu Ile Val Leu His Tyr Pro Tyr Ile
                100                 105                 110

Pro Pro Gly Glu Lys Glu Ala Ser Leu Ala Lys Ile Lys Asp Lys Ala
            115                 120                 125

Arg Asn Arg Tyr Phe Pro Ala Phe Glu Lys Val Leu Lys Ser His Gly
130                 135                 140

Gln Asp Tyr Leu Val Gly Asn Arg Leu Ser Arg Ala Asp Val Tyr Leu
145                 150                 155                 160

Val Gln Val Leu Tyr His Val Glu Glu Leu Asp Pro Ser Ala Leu Ala
                165                 170                 175

Asn Phe Pro Leu Leu Lys Ala Leu Arg Thr Arg Val Ser Asn Leu Pro
            180                 185                 190

Thr Val Lys Lys Phe Leu Gln Pro Gly Ser Gln Arg Lys Pro Leu Glu
        195                 200                 205

Asp Glu Lys Cys Val Glu Ser Ala Val Lys Ile Phe Ser
210                 215                 220
```

(2) INFORMATION FOR SEQ ID NO:9:

(i) SEQUENCE CHARACTERISTICS:
        (A) LENGTH: 959 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (B) STRAIN: 9-11s9

(ix) FEATURE:
        (A) NAME/KEY: CDS
        (B) LOCATION: 45..710

(xi) SEQUENCE DESCRIPTION: SEQ ID NO:9:

```
AGAGGGAGCA GCTTTTTAAC AAGAGAACTC AAGCAATTGC TGCC ATG CCG GGG AAG      56
                                                 Met Pro Gly Lys
                                                   1

CCA GTA CTT CAC TAC GTG CGC ATC AGG GGG AGA ATG GAG CCC ATC CGG     104
Pro Val Leu His Tyr Val Arg Ile Arg Gly Arg Met Glu Pro Ile Arg
  5                  10                  15                  20

TGG CTC CTG GCT GCA GCT GGA GTA GAG TTT GAA GAA CAA TTT CTG AAA     152
Trp Leu Leu Ala Ala Ala Gly Val Glu Phe Glu Glu Gln Phe Leu Lys
                 25                  30                  35

ACT CGG GAT GAC CTG GCC AGG CTA AGG AAT GAT GGG AGT TTG ATG TTC     200
Thr Arg Asp Asp Leu Ala Arg Leu Arg Asn Asp Gly Ser Leu Met Phe
             40                  45                  50

CAG CAA GTG CCC ATG GTG GAG ATT GAT GGG ATG AAG CTG GTG CAG ACC     248
Gln Gln Val Pro Met Val Glu Ile Asp Gly Met Lys Leu Val Gln Thr
         55                  60                  65

AGA GCC ATT CTC AAC TAC ATT GCC ACC AAA TAC AAC CTC TAT GGG AAG     296
Arg Ala Ile Leu Asn Tyr Ile Ala Thr Lys Tyr Asn Leu Tyr Gly Lys
     70                  75                  80
```

```
GAC ATG AAG GAG AGA GCC CTC ATC GAC ATG TAT GCA GAA GGA GTG GCG        344
Asp Met Lys Glu Arg Ala Leu Ile Asp Met Tyr Ala Glu Gly Val Ala
 85              90                  95                 100

GAT CTG GAT GAA ATA GTT CTC CAT TAC CCT TAC ATT CCC CCT GGG GAG        392
Asp Leu Asp Glu Ile Val Leu His Tyr Pro Tyr Ile Pro Pro Gly Glu
                105                 110                 115

AAA GAG GCA AGT CTT GCC AAA ATC AAG GAC AAA GCA AGG AAC CGT TAC        440
Lys Glu Ala Ser Leu Ala Lys Ile Lys Asp Lys Ala Arg Asn Arg Tyr
            120                 125                 130

TTT CCT GCC TTT GAA AAG GTG TTG AAG AGC CAT GGA CAA GAT TAT CTC        488
Phe Pro Ala Phe Glu Lys Val Leu Lys Ser His Gly Gln Asp Tyr Leu
        135                 140                 145

GTT GGC AAT AGG CTG AGC AGA GCT GAT GTT TAC CTA GTT CAA GTT CTC        536
Val Gly Asn Arg Leu Ser Arg Ala Asp Val Tyr Leu Val Gln Val Leu
    150                 155                 160

TAC CAT GTG GAA GAG CTG GAC CCC AGC GCT TTG GCC AAC TTC CCT CTG        584
Tyr His Val Glu Glu Leu Asp Pro Ser Ala Leu Ala Asn Phe Pro Leu
165                 170                 175                 180

CTG AAG GCC CTG AGA ACC AGA GTC AGC AAC CTC CCC ACA GTG AAG AAG        632
Leu Lys Ala Leu Arg Thr Arg Val Ser Asn Leu Pro Thr Val Lys Lys
                185                 190                 195

TTT CTT CAG CCT GGC AGC CAG AGG AAG CCA TTA GAG GAT GAG AAA TGT        680
Phe Leu Gln Pro Gly Ser Gln Arg Lys Pro Leu Glu Asp Glu Lys Cys
            200                 205                 210

GTA GAA TCT GCA GTT AAG ATC TTC AGT TAATTCAGGC ATCTATGGAT              727
Val Glu Ser Ala Val Lys Ile Phe Ser
        215                 220

ACACTGTACC CACAAAGCCA GCCTTCGAAA GCTTTGCAAC AATCGCATAT TTTGACTAAA      787

TGTTGACCCT ACTTATTGGG AGGCCAACAC GTTTTCTAAT GCTTCTGTGT TAATTCATAT      847

AGACATGACT GATGAGGAAT TGCTGGGATG CTATTTGGTT GTAGTTAAAA TTTGAAATCA      907

TGATCACTTC CTCAGATATT ACTTTGAATC TCAATAAAAA CTTCGCAAGC TT             959

(2) INFORMATION FOR SEQ ID NO:10:

(i) SEQUENCE CHARACTERISTICS:
        (A) LENGTH: 221 amino acids
        (B) TYPE: amino acid
        (D) TOPOLOGY: linear (ii) MOLECULE TYPE: protein (xi) SEQUENCE DESCRIPTION: SEQ ID NO:10:

Met Pro Gly Lys Pro Val Leu His Tyr Val Arg Ile Arg Gly Arg Met
 1               5                  10                  15

Glu Pro Ile Arg Trp Leu Leu Ala Ala Ala Gly Val Glu Phe Glu Glu
                20                  25                  30

Gln Phe Leu Lys Thr Arg Asp Asp Leu Ala Arg Leu Arg Asn Asp Gly
            35                  40                  45

Ser Leu Met Phe Gln Gln Val Pro Met Val Glu Ile Asp Gly Met Lys
        50                  55                  60

Leu Val Gln Thr Arg Ala Ile Leu Asn Tyr Ile Ala Thr Lys Tyr Asn
65                  70                  75                  80

Leu Tyr Gly Lys Asp Met Lys Glu Arg Ala Leu Ile Asp Met Tyr Ala
                85                  90                  95

Glu Gly Val Ala Asp Leu Asp Glu Ile Val Leu His Tyr Pro Tyr Ile
            100                 105                 110

Pro Pro Gly Glu Lys Glu Ala Ser Leu Ala Lys Ile Lys Asp Lys Ala
```

```
                 115                 120                 125
Arg Asn Arg Tyr Phe Pro Ala Phe Glu Lys Val Leu Lys Ser His Gly
    130                 135                 140

Gln Asp Tyr Leu Val Gly Asn Arg Leu Ser Arg Ala Asp Val Tyr Leu
145                 150                 155                 160

Val Gln Val Leu Tyr His Val Glu Glu Leu Asp Pro Ser Ala Leu Ala
                165                 170                 175

Asn Phe Pro Leu Leu Lys Ala Leu Arg Thr Arg Val Ser Asn Leu Pro
            180                 185                 190

Thr Val Lys Lys Phe Leu Gln Pro Gly Ser Gln Arg Lys Pro Leu Glu
        195                 200                 205

Asp Glu Lys Cys Val Glu Ser Ala Val Lys Ile Phe Ser
    210                 215                 220

(2) INFORMATION FOR SEQ ID NO:11:

(i) SEQUENCE CHARACTERISTICS:
        (A) LENGTH: 959 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (B) STRAIN: 9-11s15

(ix) FEATURE:
        (A) NAME/KEY: CDS
        (B) LOCATION: 45..710

(xi) SEQUENCE DESCRIPTION: SEQ ID NO:11:

AGAGGGAGCA GCTTTTTAAC AAGAGAACTC AAGCAATTGC TGCC ATG CCG GGG AAG        56
                                                Met Pro Gly Lys

CCA GTA CTT CAC TAC GGG ATC TTG AGG GGG AGA ATG GAG CCC ATC CGG       104
Pro Val Leu His Tyr Gly Ile Leu Arg Gly Arg Met Glu Pro Ile Arg
  5                  10                  15                  20

TGG CTC CTG GCT GCA GCT GGA GTA GAG TTT GAA GAA CAA TTT CTG AAA       152
Trp Leu Leu Ala Ala Ala Gly Val Glu Phe Glu Glu Gln Phe Leu Lys
                 25                  30                  35

ACT CGG GAT GAC CTG GCC AGG CTA AGG AAT GAT GGG AGT TTG ATG TTC       200
Thr Arg Asp Asp Leu Ala Arg Leu Arg Asn Asp Gly Ser Leu Met Phe
             40                  45                  50

CAG CAA GTG CCC ATG GTG GAG ATT GAT GGG ATG AAG CTG GTG CAG ACC       248
Gln Gln Val Pro Met Val Glu Ile Asp Gly Met Lys Leu Val Gln Thr
         55                  60                  65

AGA GCC ATT CTC AAC TAC ATT GCC ACC AAA TAC AAC CTC TAT GGG AAG       296
Arg Ala Ile Leu Asn Tyr Ile Ala Thr Lys Tyr Asn Leu Tyr Gly Lys
     70                  75                  80

GAC ATG AAG GAG AGA GCC CTC ATC GAC ATG TAT GCA GAA GGA GTG GCG       344
Asp Met Lys Glu Arg Ala Leu Ile Asp Met Tyr Ala Glu Gly Val Ala
 85                  90                  95                 100

GAT CTG GAT GAA ATA GTT CTC CAT TAC CCT TAC ATT CCC CCT GGG GAG       392
Asp Leu Asp Glu Ile Val Leu His Tyr Pro Tyr Ile Pro Pro Gly Glu
                105                 110                 115

AAA GAG GCA AGT CTT GCC AAA ATC AAG GAC AAA GCA AGG AAC CGT TAC       440
Lys Glu Ala Ser Leu Ala Lys Ile Lys Asp Lys Ala Arg Asn Arg Tyr
            120                 125                 130

TTT CCT GCC TTT GAA AAG GTG TTG AAG AGC CAT GGA CAA GAT TAT CTC       488
Phe Pro Ala Phe Glu Lys Val Leu Lys Ser His Gly Gln Asp Tyr Leu
        135                 140                 145
```

```
GTT GGC AAT AGG CTG AGC AGA GCT GAT GTT TAC CTA GTT CAA GTT CTC      536
Val Gly Asn Arg Leu Ser Arg Ala Asp Val Tyr Leu Val Gln Val Leu
    150                 155                 160

TAC CAT GTG GAA GAG CTG GAC CCC AGC GCT TTG GCC AAC TTC CCT CTG      584
Tyr His Val Glu Glu Leu Asp Pro Ser Ala Leu Ala Asn Phe Pro Leu
165                 170                 175                 180

CTG AAG GCC CTG AGA ACC AGA GTC AGC AAC CTC CCC ACA GTG AAG AAG      632
Leu Lys Ala Leu Arg Thr Arg Val Ser Asn Leu Pro Thr Val Lys Lys
                185                 190                 195

TTT CTT CAG CCT GGC AGC CAG AGG AAG CCA TTA GAG GAT GAG AAA TGT      680
Phe Leu Gln Pro Gly Ser Gln Arg Lys Pro Leu Glu Asp Glu Lys Cys
            200                 205                 210

GTA GAA TCT GCA GTT AAG ATC TTC AGT TAATTCAGGC ATCTATGGAT            727
Val Glu Ser Ala Val Lys Ile Phe Ser
        215                 220

ACACTGTACC CACAAAGCCA GCCTTCGAAA GCTTTGCAAC AATCGCATAT TTTGACTAAA    787

TGTTGACCCT ACTTATTGGG AGGCCAACAC GTTTTCTAAT GCTTCTGTGT TAATTCATAT    847

AGACATGACT GATGAGGAAT TGCTGGGATG CTATTTGGTT GTAGTTAAAA TTTGAAATCA    907

TGATCACTTC CTCAGATATT ACTTTGAATC TCAATAAAAA CTTCGCAAGC TT           959

(2) INFORMATION FOR SEQ ID NO:12:

(i) SEQUENCE CHARACTERISTICS:
        (A) LENGTH: 221 amino acids
        (B) TYPE: amino acid
        (D) TOPOLOGY: linear (ii) MOLECULE TYPE: protein (xi) SEQUENCE DESCRIPTION: SEQ ID NO:12:

Met Pro Gly Lys Pro Val Leu His Tyr Gly Ile Leu Arg Gly Arg Met
1               5                   10                  15

Glu Pro Ile Arg Trp Leu Leu Ala Ala Gly Val Glu Phe Glu Glu
            20                  25                  30

Gln Phe Leu Lys Thr Arg Asp Asp Leu Ala Arg Leu Arg Asn Asp Gly
        35                  40                  45

Ser Leu Met Phe Gln Gln Val Pro Met Val Glu Ile Asp Gly Met Lys
    50                  55                  60

Leu Val Gln Thr Arg Ala Ile Leu Asn Tyr Ile Ala Thr Lys Tyr Asn
65                  70                  75                  80

Leu Tyr Gly Lys Asp Met Lys Glu Arg Ala Leu Ile Asp Met Tyr Ala
                85                  90                  95

Glu Gly Val Ala Asp Leu Asp Glu Ile Val Leu His Tyr Pro Tyr Ile
            100                 105                 110

Pro Pro Gly Glu Lys Glu Ala Ser Leu Ala Lys Ile Lys Asp Lys Ala
        115                 120                 125

Arg Asn Arg Tyr Phe Pro Ala Phe Glu Lys Val Leu Lys Ser His Gly
    130                 135                 140

Gln Asp Tyr Leu Val Gly Asn Arg Leu Ser Arg Ala Asp Val Tyr Leu
145                 150                 155                 160

Val Gln Val Leu Tyr His Val Glu Glu Leu Asp Pro Ser Ala Leu Ala
                165                 170                 175

Asn Phe Pro Leu Leu Lys Ala Leu Arg Thr Arg Val Ser Asn Leu Pro
            180                 185                 190

Thr Val Lys Lys Phe Leu Gln Pro Gly Ser Gln Arg Lys Pro Leu Glu
        195                 200                 205
```

Asp Glu Lys Cys Val Glu Ser Ala Val Lys Ile Phe Ser
    210             215                 220

(2) INFORMATION FOR SEQ ID NO:13:

(i) SEQUENCE CHARACTERISTICS:
       (A) LENGTH: 959 base pairs
       (B) TYPE: nucleic acid
       (C) STRANDEDNESS: double
       (D) TOPOLOGY: linear (ii) MOLECULE TYPE: DNA (genomic)

(vi) ORIGINAL SOURCE:
       (B) STRAIN: 9-11s16

(ix) FEATURE:
       (A) NAME/KEY: CDS
       (B) LOCATION: 45..710

(xi) SEQUENCE DESCRIPTION: SEQ ID NO:13:

```
AGAGGGAGCA GCTTTTTAAC AAGAGAACTC AAGCAATTGC TGCC ATG CCG GGG AAG        56
                                                  Met Pro Gly Lys
                                                   1

CCA GTA CTT CAC TAC GTC CCC CTC AGG GGG AGA ATG GAG CCC ATC CGG       104
Pro Val Leu His Tyr Val Pro Leu Arg Gly Arg Met Glu Pro Ile Arg
  5              10                  15                  20

TGG CTC CTG GCT GCA GCT GGA GTA GAG TTT GAA GAA CAA TTT CTG AAA       152
Trp Leu Leu Ala Ala Ala Gly Val Glu Phe Glu Glu Gln Phe Leu Lys
                 25                  30                  35

ACT CGG GAT GAC CTG GCC AGG CTA AGG AAT GAT GGG AGT TTG ATG TTC       200
Thr Arg Asp Asp Leu Ala Arg Leu Arg Asn Asp Gly Ser Leu Met Phe
             40                  45                  50

CAG CAA GTG CCC ATG GTG GAG ATT GAT GGG ATG AAG CTG GTG CAG ACC       248
Gln Gln Val Pro Met Val Glu Ile Asp Gly Met Lys Leu Val Gln Thr
         55                  60                  65

AGA GCC ATT CTC AAC TAC ATT GCC ACC AAA TAC AAC CTC TAT GGG AAG       296
Arg Ala Ile Leu Asn Tyr Ile Ala Thr Lys Tyr Asn Leu Tyr Gly Lys
     70                  75                  80

GAC ATG AAG GAG AGA GCC CTC ATC GAC ATG TAT GCA GAA GGA GTG GCG       344
Asp Met Lys Glu Arg Ala Leu Ile Asp Met Tyr Ala Glu Gly Val Ala
 85                  90                  95                 100

GAT CTG GAT GAA ATA GTT CTC CAT TAC CCT TAC ATT CCC CCT GGG GAG       392
Asp Leu Asp Glu Ile Val Leu His Tyr Pro Tyr Ile Pro Pro Gly Glu
                105                 110                 115

AAA GAG GCA AGT CTT GCC AAA ATC AAG GAC AAA GCA AGG AAC CGT TAC       440
Lys Glu Ala Ser Leu Ala Lys Ile Lys Asp Lys Ala Arg Asn Arg Tyr
            120                 125                 130

TTT CCT GCC TTT GAA AAG GTG TTG AAG AGC CAT GGA CAA GAT TAT CTC       488
Phe Pro Ala Phe Glu Lys Val Leu Lys Ser His Gly Gln Asp Tyr Leu
        135                 140                 145

GTT GGC AAT AGG CTG AGC AGA GCT GAT GTT TAC CTA GTT CAA GTT CTC       536
Val Gly Asn Arg Leu Ser Arg Ala Asp Val Tyr Leu Val Gln Val Leu
    150                 155                 160

TAC CAT GTG GAA GAG CTG GAC CCC AGC GCT TTG GCC AAC TTC CCT CTG       584
Tyr His Val Glu Glu Leu Asp Pro Ser Ala Leu Ala Asn Phe Pro Leu
165                 170                 175                 180

CTG AAG GCC CTG AGA ACC AGA GTC AGC AAC CTC CCC ACA GTG AAG AAG       632
Leu Lys Ala Leu Arg Thr Arg Val Ser Asn Leu Pro Thr Val Lys Lys
                185                 190                 195

TTT CTT CAG CCT GGC AGC CAG AGG AAG CCA TTA GAG GAT GAG AAA TGT       680
Phe Leu Gln Pro Gly Ser Gln Arg Lys Pro Leu Glu Asp Glu Lys Cys
            200                 205                 210
```

```
GTA GAA TCT GCA GTT AAG ATC TTC AGT TAATTCAGGC ATCTATGGAT          727
Val Glu Ser Ala Val Lys Ile Phe Ser
            215                 220

ACACTGTACC CACAAAGCCA GCCTTCGAAA GCTTTGCAAC AATCGCATAT TTTGACTAAA  787

TGTTGACCCT ACTTATTGGG AGGCCAACAC GTTTTCTAAT GCTTCTGTGT TAATTCATAT  847

AGACATGACT GATGAGGAAT TGCTGGGATG CTATTTGGTT GTAGTTAAAA TTTGAAATCA  907

TGATCACTTC CTCAGATATT ACTTTGAATC TCAATAAAAA CTTCGCAAGC TT          959
```

(2) INFORMATION FOR SEQ ID NO:14:

(i) SEQUENCE CHARACTERISTICS:
        (A) LENGTH: 221 amino acids
        (B) TYPE: amino acid
        (D) TOPOLOGY: linear (ii) MOLECULE TYPE: protein (xi) SEQUENCE DESCRIPTION: SEQ ID NO:14:

```
Met Pro Gly Lys Pro Val Leu His Tyr Val Pro Leu Arg Gly Arg Met
 1               5                  10                  15

Glu Pro Ile Arg Trp Leu Leu Ala Ala Ala Gly Val Glu Phe Glu Glu
            20                  25                  30

Gln Phe Leu Lys Thr Arg Asp Asp Leu Ala Arg Leu Arg Asn Asp Gly
        35                  40                  45

Ser Leu Met Phe Gln Gln Val Pro Met Val Glu Ile Asp Gly Met Lys
    50                  55                  60

Leu Val Gln Thr Arg Ala Ile Leu Asn Tyr Ile Ala Thr Lys Tyr Asn
65                  70                  75                  80

Leu Tyr Gly Lys Asp Met Lys Glu Arg Ala Leu Ile Asp Met Tyr Ala
                85                  90                  95

Glu Gly Val Ala Asp Leu Asp Glu Ile Val Leu His Tyr Pro Tyr Ile
            100                 105                 110

Pro Pro Gly Glu Lys Glu Ala Ser Leu Ala Lys Ile Lys Asp Lys Ala
        115                 120                 125

Arg Asn Arg Tyr Phe Pro Ala Phe Glu Lys Val Leu Lys Ser His Gly
    130                 135                 140

Gln Asp Tyr Leu Val Gly Asn Arg Leu Ser Arg Ala Asp Val Tyr Leu
145                 150                 155                 160

Val Gln Val Leu Tyr His Val Glu Glu Leu Asp Pro Ser Ala Leu Ala
                165                 170                 175

Asn Phe Pro Leu Leu Lys Ala Leu Arg Thr Arg Val Ser Asn Leu Pro
            180                 185                 190

Thr Val Lys Lys Phe Leu Gln Pro Gly Ser Gln Arg Lys Pro Leu Glu
        195                 200                 205

Asp Glu Lys Cys Val Glu Ser Ala Val Lys Ile Phe Ser
    210                 215                 220
```

(2) INFORMATION FOR SEQ ID NO:15:

(i) SEQUENCE CHARACTERISTICS:
        (A) LENGTH: 959 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (B) STRAIN: 9-11s21

(ix) FEATURE:
    (A) NAME/KEY: CDS
    (B) LOCATION: 45..710

(xi) SEQUENCE DESCRIPTION: SEQ ID NO:15:

```
AGAGGGAGCA GCTTTTTAAC AAGAGAACTC AAGCAATTGC TGCC ATG CCG GGG AAG      56
                                                 Met Pro Gly Lys
                                                  1

CCA GTA CTT CAC TAC GTG ATC TGC AGG GGG AGA ATG GAG CCC ATC CGG     104
Pro Val Leu His Tyr Val Ile Cys Arg Gly Arg Met Glu Pro Ile Arg
  5              10                  15                  20

TGG CTC CTG GCT GCA GCT GGA GTA GAG TTT GAA GAA CAA TTT CTG AAA     152
Trp Leu Leu Ala Ala Ala Gly Val Glu Phe Glu Glu Gln Phe Leu Lys
             25                  30                  35

ACT CGG GAT GAC CTG GCC AGG CTA AGG AAT GAT GGG AGT TTG ATG TTC     200
Thr Arg Asp Asp Leu Ala Arg Leu Arg Asn Asp Gly Ser Leu Met Phe
         40                  45                  50

CAG CAA GTG CCC ATG GTG GAG ATT GAT GGG ATG AAG CTG GTG CAG ACC     248
Gln Gln Val Pro Met Val Glu Ile Asp Gly Met Lys Leu Val Gln Thr
     55                  60                  65

AGA GCC ATT CTC AAC TAC ATT GCC ACC AAA TAC AAC CTC TAT GGG AAG     296
Arg Ala Ile Leu Asn Tyr Ile Ala Thr Lys Tyr Asn Leu Tyr Gly Lys
 70                  75                  80

GAC ATG AAG GAG AGA GCC CTC ATC GAC ATG TAT GCA GAA GGA GTG GCG     344
Asp Met Lys Glu Arg Ala Leu Ile Asp Met Tyr Ala Glu Gly Val Ala
 85                  90                  95                 100

GAT CTG GAT GAA ATA GTT CTC CAT TAC CCT TAC ATT CCC CCT GGG GAG     392
Asp Leu Asp Glu Ile Val Leu His Tyr Pro Tyr Ile Pro Pro Gly Glu
                105                 110                 115

AAA GAG GCA AGT CTT GCC AAA ATC AAG GAC AAA GCA AGG AAC CGT TAC     440
Lys Glu Ala Ser Leu Ala Lys Ile Lys Asp Lys Ala Arg Asn Arg Tyr
            120                 125                 130

TTT CCT GCC TTT GAA AAG GTG TTG AAG AGC CAT GGA CAA GAT TAT CTC     488
Phe Pro Ala Phe Glu Lys Val Leu Lys Ser His Gly Gln Asp Tyr Leu
        135                 140                 145

GTT GGC AAT AGG CTG AGC AGA GCT GAT GTT TAC CTA GTT CAA GTT CTC     536
Val Gly Asn Arg Leu Ser Arg Ala Asp Val Tyr Leu Val Gln Val Leu
    150                 155                 160

TAC CAT GTG GAA GAG CTG GAC CCC AGC GCT TTG GCC AAC TTC CCT CTG     584
Tyr His Val Glu Glu Leu Asp Pro Ser Ala Leu Ala Asn Phe Pro Leu
165                 170                 175                 180

CTG AAG GCC CTG AGA ACC AGA GTC AGC AAC CTC CCC ACA GTG AAG AAG     632
Leu Lys Ala Leu Arg Thr Arg Val Ser Asn Leu Pro Thr Val Lys Lys
                185                 190                 195

TTT CTT CAG CCT GGC AGC CAG AGG AAG CCA TTA GAG GAT GAG AAA TGT     680
Phe Leu Gln Pro Gly Ser Gln Arg Lys Pro Leu Glu Asp Glu Lys Cys
            200                 205                 210

GTA GAA TCT GCA GTT AAG ATC TTC AGT TAATTCAGGC ATCTATGGAT           727
Val Glu Ser Ala Val Lys Ile Phe Ser
            215                 220

ACACTGTACC CACAAAGCCA GCCTTCGAAA GCTTTGCAAC AATCGCATAT TTTGACTAAA   787

TGTTGACCCT ACTTATTGGG AGGCCAACAC GTTTTCTAAT GCTTCTGTGT TAATTCATAT   847

AGACATGACT GATGAGGAAT TGCTGGGATG CTATTTGGTT GTAGTTAAAA TTTGAAATCA   907

TGATCACTTC CTCAGATATT ACTTTGAATC TCAATAAAAA CTTCGCAAGC TT           959
```

(2) INFORMATION FOR SEQ ID NO:16:

(i) SEQUENCE CHARACTERISTICS:

(A) LENGTH: 221 amino acids
        (B) TYPE: amino acid
        (D) TOPOLOGY: linear (ii) MOLECULE TYPE: protein (xi) SEQUENCE DESCRIPTION: SEQ ID NO:16:

Met Pro Gly Lys Pro Val Leu His Tyr Val Ile Cys Arg Gly Arg Met
 1               5                  10                  15

Glu Pro Ile Arg Trp Leu Leu Ala Ala Ala Gly Val Glu Phe Glu Glu
             20                  25                  30

Gln Phe Leu Lys Thr Arg Asp Asp Leu Ala Arg Leu Arg Asn Asp Gly
         35                  40                  45

Ser Leu Met Phe Gln Gln Val Pro Met Val Glu Ile Asp Gly Met Lys
 50                  55                  60

Leu Val Gln Thr Arg Ala Ile Leu Asn Tyr Ile Ala Thr Lys Tyr Asn
65                  70                  75                  80

Leu Tyr Gly Lys Asp Met Lys Glu Arg Ala Leu Ile Asp Met Tyr Ala
                 85                  90                  95

Glu Gly Val Ala Asp Leu Asp Glu Ile Val Leu His Tyr Pro Tyr Ile
            100                 105                 110

Pro Pro Gly Glu Lys Glu Ala Ser Leu Ala Lys Ile Lys Asp Lys Ala
        115                 120                 125

Arg Asn Arg Tyr Phe Pro Ala Phe Glu Lys Val Leu Lys Ser His Gly
    130                 135                 140

Gln Asp Tyr Leu Val Gly Asn Arg Leu Ser Arg Ala Asp Val Tyr Leu
145                 150                 155                 160

Val Gln Val Leu Tyr His Val Glu Glu Leu Asp Pro Ser Ala Leu Ala
                165                 170                 175

Asn Phe Pro Leu Leu Lys Ala Leu Arg Thr Arg Val Ser Asn Leu Pro
            180                 185                 190

Thr Val Lys Lys Phe Leu Gln Pro Gly Ser Gln Arg Lys Pro Leu Glu
        195                 200                 205

Asp Glu Lys Cys Val Glu Ser Ala Val Lys Ile Phe Ser
    210                 215                 220

(2) INFORMATION FOR SEQ ID NO:17:

(i) SEQUENCE CHARACTERISTICS:
        (A) LENGTH: 959 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (B) STRAIN: 9-11s22

(ix) FEATURE:
        (A) NAME/KEY: CDS
        (B) LOCATION: 45..710

(xi) SEQUENCE DESCRIPTION: SEQ ID NO:17:

AGAGGGAGCA GCTTTTTAAC AAGAGAACTC AAGCAATTGC TGCC ATG CCG GGG AAG      56
                                               Met Pro Gly Lys
                                                1

CCA GTA CTT CAC TAC TGC GAC ATC AGG GGG AGA ATG GAG CCC ATC CGG     104
Pro Val Leu His Tyr Cys Asp Ile Arg Gly Arg Met Glu Pro Ile Arg
 5                  10                  15                  20

TGG CTC CTG GCT GCA GCT GGA GTA GAG TTT GAA GAA CAA TTT CTG AAA     152

```
Trp Leu Ala Ala Ala Gly Val Glu Phe Glu Glu Gln Phe Leu Lys
            25                  30                  35

ACT CGG GAT GAC CTG GCC AGG CTA AGG AAT GAT GGG AGT TTG ATG TTC        200
Thr Arg Asp Asp Leu Ala Arg Leu Arg Asn Asp Gly Ser Leu Met Phe
        40                  45                  50

CAG CAA GTG CCC ATG GTG GAG ATT GAT GGG ATG AAG CTG GTG CAG ACC        248
Gln Gln Val Pro Met Val Glu Ile Asp Gly Met Lys Leu Val Gln Thr
    55                  60                  65

AGA GCC ATT CTC AAC TAC ATT GCC ACC AAA TAC AAC CTC TAT GGG AAG        296
Arg Ala Ile Leu Asn Tyr Ile Ala Thr Lys Tyr Asn Leu Tyr Gly Lys
70                  75                  80

GAC ATG AAG GAG AGA GCC CTC ATC GAC ATG TAT GCA GAA GGA GTG GCG        344
Asp Met Lys Glu Arg Ala Leu Ile Asp Met Tyr Ala Glu Gly Val Ala
85                  90                  95                  100

GAT CTG GAT GAA ATA GTT CTC CAT TAC CCT TAC ATT CCC CCT GGG GAG        392
Asp Leu Asp Glu Ile Val Leu His Tyr Pro Tyr Ile Pro Pro Gly Glu
            105                 110                 115

AAA GAG GCA AGT CTT GCC AAA ATC AAG GAC AAA GCA AGG AAC CGT TAC        440
Lys Glu Ala Ser Leu Ala Lys Ile Lys Asp Lys Ala Arg Asn Arg Tyr
        120                 125                 130

TTT CCT GCC TTT GAA AAG GTG TTG AAG AGC CAT GGA CAA GAT TAT CTC        488
Phe Pro Ala Phe Glu Lys Val Leu Lys Ser His Gly Gln Asp Tyr Leu
    135                 140                 145

GTT GGC AAT AGG CTG AGC AGA GCT GAT GTT TAC CTA GTT CAA GTT CTC        536
Val Gly Asn Arg Leu Ser Arg Ala Asp Val Tyr Leu Val Gln Val Leu
150                 155                 160

TAC CAT GTG GAA GAG CTG GAC CCC AGC GCT TTG GCC AAC TTC CCT CTG        584
Tyr His Val Glu Glu Leu Asp Pro Ser Ala Leu Ala Asn Phe Pro Leu
165                 170                 175                 180

CTG AAG GCC CTG AGA ACC AGA GTC AGC AAC CTC CCC ACA GTG AAG AAG        632
Leu Lys Ala Leu Arg Thr Arg Val Ser Asn Leu Pro Thr Val Lys Lys
            185                 190                 195

TTT CTT CAG CCT GGC AGC CAG AGG AAG CCA TTA GAG GAT GAG AAA TGT        680
Phe Leu Gln Pro Gly Ser Gln Arg Lys Pro Leu Glu Asp Glu Lys Cys
        200                 205                 210

GTA GAA TCT GCA GTT AAG ATC TTC AGT TAATTCAGGC ATCTATGGAT             727
Val Glu Ser Ala Val Lys Ile Phe Ser
    215                 220

ACACTGTACC CACAAAGCCA GCCTTCGAAA GCTTTGCAAC AATCGCATAT TTTGACTAAA      787

TGTTGACCCT ACTTATTGGG AGGCCAACAC GTTTTCTAAT GCTTCTGTGT TAATTCATAT      847

AGACATGACT GATGAGGAAT TGCTGGGATG CTATTTGGTT GTAGTTAAAA TTTGAAATCA      907

TGATCACTTC CTCAGATATT ACTTTGAATC TCAATAAAAA CTTCGCAAGC TT             959

(2) INFORMATION FOR SEQ ID NO:18:

(i) SEQUENCE CHARACTERISTICS:
        (A) LENGTH: 221 amino acids
        (B) TYPE: amino acid
        (D) TOPOLOGY: linear (ii) MOLECULE TYPE: protein (xi) SEQUENCE DESCRIPTION: SEQ ID NO:18:

Met Pro Gly Lys Pro Val Leu His Tyr Cys Asp Ile Arg Gly Arg Met
 1               5                  10                  15

Glu Pro Ile Arg Trp Leu Leu Ala Ala Ala Gly Val Glu Phe Glu Glu
            20                  25                  30

Gln Phe Leu Lys Thr Arg Asp Asp Leu Ala Arg Leu Arg Asn Asp Gly
        35                  40                  45
```

```
Ser Leu Met Phe Gln Gln Val Pro Met Val Glu Ile Asp Gly Met Lys
    50                  55                  60

Leu Val Gln Thr Arg Ala Ile Leu Asn Tyr Ile Ala Thr Lys Tyr Asn
 65                  70                  75                  80

Leu Tyr Gly Lys Asp Met Lys Glu Arg Ala Leu Ile Asp Met Tyr Ala
                 85                  90                  95

Glu Gly Val Ala Asp Leu Asp Glu Ile Val Leu His Tyr Pro Tyr Ile
                100                 105                 110

Pro Pro Gly Glu Lys Glu Ala Ser Leu Ala Lys Ile Lys Asp Lys Ala
                115                 120                 125

Arg Asn Arg Tyr Phe Pro Ala Phe Glu Lys Val Leu Lys Ser His Gly
130                 135                 140

Gln Asp Tyr Leu Val Gly Asn Arg Leu Ser Arg Ala Asp Val Tyr Leu
145                 150                 155                 160

Val Gln Val Leu Tyr His Val Glu Glu Leu Asp Pro Ser Ala Leu Ala
                165                 170                 175

Asn Phe Pro Leu Leu Lys Ala Leu Arg Thr Arg Val Ser Asn Leu Pro
                180                 185                 190

Thr Val Lys Lys Phe Leu Gln Pro Gly Ser Gln Arg Lys Pro Leu Glu
                195                 200                 205

Asp Glu Lys Cys Val Glu Ser Ala Val Lys Ile Phe Ser
210                 215                 220

(2) INFORMATION FOR SEQ ID NO:19:

(i) SEQUENCE CHARACTERISTICS:
        (A) LENGTH: 959 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (B) STRAIN: WCs3

(ix) FEATURE:
        (A) NAME/KEY: CDS
        (B) LOCATION: 45..710

(xi) SEQUENCE DESCRIPTION: SEQ ID NO:19:

AGAGGGAGCA GCTTTTTAAC AAGAGAACTC AAGCAATTGC TGCC ATG CCG GGG AAG        56
                                                Met Pro Gly Lys
                                                  1

CCA GTA CTT CAC TAC TTA GAT GGC AGG GGG AGA ATG GAG CCC ATC CGG       104
Pro Val Leu His Tyr Leu Asp Gly Arg Gly Arg Met Glu Pro Ile Arg
  5                  10                  15                  20

TGG CTC CTG GCT GCA GCT GGA GTA GAG TTT GAA GAA CAA TTT CTG AAA       152
Trp Leu Leu Ala Ala Ala Gly Val Glu Phe Glu Glu Gln Phe Leu Lys
                 25                  30                  35

ACT CGG GAT GAC CTG GCC AGG CTA AGG AAT GAT GGG AGT TTG ATG TTC       200
Thr Arg Asp Asp Leu Ala Arg Leu Arg Asn Asp Gly Ser Leu Met Phe
             40                  45                  50

CAG CAA GTG CCC ATG GTG GAG ATT GAT GGG ATG AAG CTG GTG CAG ACC       248
Gln Gln Val Pro Met Val Glu Ile Asp Gly Met Lys Leu Val Gln Thr
         55                  60                  65

AGA GCC ATT CTC AAC TAC ATT GCC ACC AAA TAC AAC CTC TAT GGG AAG       296
Arg Ala Ile Leu Asn Tyr Ile Ala Thr Lys Tyr Asn Leu Tyr Gly Lys
     70                  75                  80

GAC ATG AAG GAG AGA GCC CTC ATC GAC ATG TAT GCA GAA GGA GTG GCG       344
```

```
Asp Met Lys Glu Arg Ala Leu Ile Asp Met Tyr Ala Glu Gly Val Ala
 85                  90                  95                 100

GAT CTG GAT GAA ATA GTT CTC CAT TAC CCT TAC ATT CCC CCT GGG GAG       392
Asp Leu Asp Glu Ile Val Leu His Tyr Pro Tyr Ile Pro Pro Gly Glu
                105                 110                 115

AAA GAG GCA AGT CTT GCC AAA ATC AAG GAC AAA GCA AGG AAC CGT TAC       440
Lys Glu Ala Ser Leu Ala Lys Ile Lys Asp Lys Ala Arg Asn Arg Tyr
                120                 125                 130

TTT CCT GCC TTT GAA AAG GTG TTG AAG AGC CAT GGA CAA GAT TAT CTC       488
Phe Pro Ala Phe Glu Lys Val Leu Lys Ser His Gly Gln Asp Tyr Leu
                135                 140                 145

GTT GGC AAT AGG CTG AGC AGA GCT GAT GTT TAC CTA GTT CAA GTT CTC       536
Val Gly Asn Arg Leu Ser Arg Ala Asp Val Tyr Leu Val Gln Val Leu
        150                 155                 160

TAC CAT GTG GAA GAG CTG GAC CCC AGC GCT TTG GCC AAC TTC CCT CTG       584
Tyr His Val Glu Glu Leu Asp Pro Ser Ala Leu Ala Asn Phe Pro Leu
165                 170                 175                 180

CTG AAG GCC CTG AGA ACC AGA GTC AGC AAC CTC CCC ACA GTG AAG AAG       632
Leu Lys Ala Leu Arg Thr Arg Val Ser Asn Leu Pro Thr Val Lys Lys
                185                 190                 195

TTT CTT CAG CCT GGC AGC CAG AGG AAG CCA TTA GAG GAT GAG AAA TGT       680
Phe Leu Gln Pro Gly Ser Gln Arg Lys Pro Leu Glu Asp Glu Lys Cys
                200                 205                 210

GTA GAA TCT GCA GTT AAG ATC TTC AGT TAATTCAGGC ATCTATGGAT             727
Val Glu Ser Ala Val Lys Ile Phe Ser
                215                 220

ACACTGTACC CACAAAGCCA GCCTTCGAAA GCTTTGCAAC AATCGCATAT TTTGACTAAA     787

TGTTGACCCT ACTTATTGGG AGGCCAACAC GTTTTCTAAT GCTTCTGTGT TAATTCATAT     847

AGACATGACT GATGAGGAAT TGCTGGGATG CTATTTGGTT GTAGTTAAAA TTTGAAATCA     907

TGATCACTTC CTCAGATATT ACTTTGAATC TCAATAAAAA CTTCGCAAGC TT             959

(2) INFORMATION FOR SEQ ID NO:20:

(i) SEQUENCE CHARACTERISTICS:
        (A) LENGTH: 221 amino acids
        (B) TYPE: amino acid
        (D) TOPOLOGY: linear (ii) MOLECULE TYPE: protein (xi) SEQUENCE DESCRIPTION: SEQ ID NO:20:

Met Pro Gly Lys Pro Val Leu His Tyr Leu Asp Gly Arg Gly Arg Met
 1               5                  10                  15

Glu Pro Ile Arg Trp Leu Leu Ala Ala Ala Gly Val Glu Phe Glu Glu
                20                  25                  30

Gln Phe Leu Lys Thr Arg Asp Asp Leu Ala Arg Leu Arg Asn Asp Gly
         35                  40                  45

Ser Leu Met Phe Gln Gln Val Pro Met Val Glu Ile Asp Gly Met Lys
    50                  55                  60

Leu Val Gln Thr Arg Ala Ile Leu Asn Tyr Ile Ala Thr Lys Tyr Asn
65                  70                  75                  80

Leu Tyr Gly Lys Asp Met Lys Glu Arg Ala Leu Ile Asp Met Tyr Ala
                85                  90                  95

Glu Gly Val Ala Asp Leu Asp Glu Ile Val Leu His Tyr Pro Tyr Ile
                100                 105                 110

Pro Pro Gly Glu Lys Glu Ala Ser Leu Ala Lys Ile Lys Asp Lys Ala
        115                 120                 125
```

```
Arg Asn Arg Tyr Phe Pro Ala Phe Glu Lys Val Leu Lys Ser His Gly
        130                 135                 140

Gln Asp Tyr Leu Val Gly Asn Arg Leu Ser Arg Ala Asp Val Tyr Leu
145                 150                 155                 160

Val Gln Val Leu Tyr His Val Glu Glu Leu Asp Pro Ser Ala Leu Ala
                165                 170                 175

Asn Phe Pro Leu Leu Lys Ala Leu Arg Thr Arg Val Ser Asn Leu Pro
            180                 185                 190

Thr Val Lys Lys Phe Leu Gln Pro Gly Ser Gln Arg Lys Pro Leu Glu
        195                 200                 205

Asp Glu Lys Cys Val Glu Ser Ala Val Lys Ile Phe Ser
210                 215                 220
```

(2) INFORMATION FOR SEQ ID NO:21:

(i) SEQUENCE CHARACTERISTICS:
        (A) LENGTH: 785 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: RBS
        (B) LOCATION: 1..3

(ix) FEATURE:
        (A) NAME/KEY: misc_signal
        (B) LOCATION: 13..96
        (D) OTHER INFORMATION: /function= "rat glucocorticoid
            receptor nuclear localization signal"

(xi) SEQUENCE DESCRIPTION: SEQ ID NO:21:

```
ACCATGGGTA CCTATCGGAA ATGTCTTCAG GCTGGAATGA ACCTTGAAGC TCGAAAAACA      60

AAGAAAAAAA TCAAAGGGAT TCAGCAAGCC ACTGCAGGTA CCGCTAGCCC GGGGAAGCCA     120

GTCCTTCACT ACTTCGATGG CAGGGGGAGA ATGGAGCCCA TCCGGTGGCT CCTGGCTGCA     180

GCTGGAGTAG AGTTTGAAGA ACAATTTCTG AAAACTCGGG ATGACCTGGC CAGGCTAAGG     240

AATGATGGGA GTTTGATGTT CCAGCAAGTG CCCATGGTGG AGATTGATGG GATGAAGCTG     300

GTGCAGACCA GAGCCATTCT CAACTACATT GCCACCAAAT ACAACCTCTA TGGGAAGGAC     360

ATGAAGGAGA GAGCCCTCAT CGACATGTAT GCAGAAGGAG TGGCGGATCT GGATGAAATA     420

GTTCTCCATT ACCCTTACAT TCCCCCTGGG GAGAAAGAGG CAAGTCTTGC CAAAATCAAG     480

GACAAAGCAA GGAACCGTTA CTTTCCTGCC TTTGAAAAGG TGTTGAAGAG CCATGGACAA     540

GATTATCTCG TTGGCAATAG GCTGAGCAGA GCTGATGTTT ACCTAGTTCA AGTTCTCTAC     600

CATGTGGAAG AGCTGGACCC CAGCGCTTTG GCCAACTTCC CTCTGCTGAA GGCCCTGAGA     660

ACCAGAGTCA GCAACCTCCC CACAGTGAAG AAGTTTCTTC AGCCTGGCAG CCAGAGGAAG     720

CCATTAGAGG ATGAGAAATG TGTAGAATCT GCAGTTAAGA TCTTCAGTTA ACTCGAGGCG     780

GCCGC                                                                 785
```

(2) INFORMATION FOR SEQ ID NO:22:

(i) SEQUENCE CHARACTERISTICS:
        (A) LENGTH: 722 base pairs
        (B) TYPE: nucleic acid
        (C) STRANDEDNESS: double
        (D) TOPOLOGY: linear (ii) MOLECULE TYPE: DNA (genomic)

(ix) FEATURE:
    (A) NAME/KEY: misc_signal
    (B) LOCATION: 13..33
    (D) OTHER INFORMATION: /function= "SV40 Large T Antigen
        nuclear localization signal"

(ix) FEATURE:
    (A) NAME/KEY: RBS
    (B) LOCATION: 1..3

(xi) SEQUENCE DESCRIPTION: SEQ ID NO:22:

```
ACCATGGGTA CCCCAAAAAA GAAGAGAAAG GTAGGTACCG CTAGCCCGGG GAAGCCAGTC    60
CTTCACTACT TCGATGGCAG GGGGAGAATG GAGCCCATCC GGTGGCTCCT GGCTGCAGCT   120
GGAGTAGAGT TTGAAGAACA ATTTCTGAAA ACTCGGGATG ACCTGGCCAG GCTAAGGAAT   180
GATGGGAGTT TGATGTTCCA GCAAGTGCCC ATGGTGGAGA TTGATGGGAT GAAGCTGGTG   240
CAGACCAGAG CCATTCTCAA CTACATTGCC ACCAAATACA ACCTCTATGG GAAGGACATG   300
AAGGAGAGAG CCCTCATCGA CATGTATGCA GAAGGAGTGG CGGATCTGGA TGAAATAGTT   360
CTCCATTACC CTTACATTCC CCCTGGGGAG AAAGAGGCAA GTCTTGCCAA AATCAAGGAC   420
AAAGCAAGGA ACCGTTACTT TCCTGCCTTT GAAAAGGTGT TGAAGAGCCA TGGACAAGAT   480
TATCTCGTTG GCAATAGGCT GAGCAGAGCT GATGTTTACC TAGTTCAAGT TCTCTACCAT   540
GTGGAAGAGC TGGACCCCAG CGCTTTGGCC AACTTCCCTC TGCTGAAGGC CCTGAGAACC   600
AGAGTCAGCA ACCTCCCCAC AGTGAAGAAG TTTCTTCAGC CTGGCAGCCA GAGGAAGCCA   660
TTAGAGGATG AGAAATGTGT AGAATCTGCA GTTAAGATCT TCAGTTAACT CGAGGCGGCC   720
GC                                                                 722
```

(2) INFORMATION FOR SEQ ID NO:23:

(i) SEQUENCE CHARACTERISTICS:
        (A) LENGTH: 54 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..54

(xi) SEQUENCE DESCRIPTION: SEQ ID NO:23:

```
AAA GAT GGT AAA AAG AAG AAA AAG AAG TCA AAG ACA AAG TGT GTA ATT    48
Lys Asp Gly Lys Lys Lys Lys Lys Lys Ser Lys Thr Lys Cys Val Ile
  1               5                  10                  15

ATG TAA                                                            54
Met
```

(2) INFORMATION FOR SEQ ID NO:24:

(i) SEQUENCE CHARACTERISTICS:
        (A) LENGTH: 17 amino acids
        (B) TYPE: amino acid
        (D) TOPOLOGY: linear (ii) MOLECULE TYPE: protein (xi) SEQUENCE DESCRIPTION: SEQ ID NO:24:

```
Lys Asp Gly Lys Lys Lys Lys Lys Lys Ser Lys Thr Lys Cys Val Ile
  1               5                  10                  15

Met
```

(2) INFORMATION FOR SEQ ID NO:25:

(i) SEQUENCE CHARACTERISTICS:
        (A) LENGTH: 41 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: misc_signal
        (B) LOCATION: 1..41
        (D) OTHER INFORMATION: /function= "Electrophile Responsive
            Element"
            /citation= ([1])

(x) PUBLICATION INFORMATION:
        (A) AUTHORS: Friling,
        (C) JOURNAL: Proc. Natl. Acad. Sci. U.S.A.
        (D) VOLUME: 87
        (F) PAGES: 6258-6262
        (G) DATE: 1990

(xi) SEQUENCE DESCRIPTION: SEQ ID NO:25:

TAGCTTGGAA ATGACATTGC TAATGGTGAC AAAGCAACTT T                      41

(2) INFORMATION FOR SEQ ID NO:26:

(i) SEQUENCE CHARACTERISTICS:
        (A) LENGTH: 48 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Artificial Sequence (xi) SEQUENCE DESCRIPTION: SEQ ID NO:26:

CCTGGGAACG CAGTACTTCA CTACNNSNNS NNSAGGGGGA GAATGGAG               48

(2) INFORMATION FOR SEQ ID NO:27:

(i) SEQUENCE CHARACTERISTICS:
        (A) LENGTH: 46 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Artificial Sequence (xi) SEQUENCE DESCRIPTION: SEQ ID NO:27:

TCTGGATGAA ATAGTACACC ATNNSNNSNN SATTCCCCCT GGGGAG                 46

(2) INFORMATION FOR SEQ ID NO:28:

(i) SEQUENCE CHARACTERISTICS:
        (A) LENGTH: 57 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Artificial Sequence (xi) SEQUENCE DESCRIPTION: SEQ ID NO:28:

CCTGGGAAGC CAGTACTTCA CTACTTCGAT GGCAGGGGGA GAATGGAGCC CATCCGG    57

(2) INFORMATION FOR SEQ ID NO:29:

(i) SEQUENCE CHARACTERISTICS:
      (A) LENGTH: 66 base pairs
      (B) TYPE: nucleic acid
      (C) STRANDEDNESS: double
      (D) TOPOLOGY: linear (ii) MOLECULE TYPE: DNA (genomic)

(vi) ORIGINAL SOURCE:
      (A) ORGANISM: Artificial Sequence (xi) SEQUENCE DESCRIPTION: SEQ ID NO:29:

CAGAAGGAGT GGCAGATCTG GATGAAATAG TACTCCATTA CCCTTACATT CCCCCTGGGG    60

AGAAAG    66

(2) INFORMATION FOR SEQ ID NO:30:

(i) SEQUENCE CHARACTERISTICS:
      (A) LENGTH: 70 base pairs
      (B) TYPE: nucleic acid
      (C) STRANDEDNESS: double
      (D) TOPOLOGY: linear (ii) MOLECULE TYPE: DNA (genomic)

(vi) ORIGINAL SOURCE:
      (A) ORGANISM: Artificial Sequence (xi) SEQUENCE DESCRIPTION: SEQ ID NO:30:

GAGGAAGCCA CTCGAGGATG AGAAATGTGT AGAATCTGCA GTTAAGATCT TCAGTTAAAG    60

GATCCTCTAG    70

(2) INFORMATION FOR SEQ ID NO:31:

(i) SEQUENCE CHARACTERISTICS:
      (A) LENGTH: 220 amino acids
      (B) TYPE: amino acid
      (D) TOPOLOGY: linear (ii) MOLECULE TYPE: protein (xi) SEQUENCE DESCRIPTION: SEQ ID NO:31:

```
Pro Gly Lys Pro Val Leu His Tyr Phe Asp Gly Arg Gly Arg Met Glu
  1               5                  10                  15

Pro Ile Arg Trp Leu Leu Ala Ala Ala Gly Val Glu Phe Glu Glu Gln
                 20                  25                  30

Phe Leu Lys Thr Arg Asp Asp Leu Ala Arg Leu Arg Asn Asp Gly Ser
             35                  40                  45

Leu Met Phe Gln Gln Val Pro Met Val Glu Ile Asp Gly Met Lys Leu
         50                  55                  60

Val Gln Thr Arg Ala Ile Leu Asn Tyr Ile Ala Thr Lys Tyr Asn Leu
 65                  70                  75                  80

Tyr Gly Lys Asp Met Lys Glu Arg Ala Leu Ile Asp Met Tyr Ala Glu
                 85                  90                  95

Gly Val Ala Asp Leu Asp Glu Ile Val Leu His Tyr Pro Tyr Ile Pro
            100                 105                 110

Pro Gly Glu Lys Glu Ala Ser Leu Ala Lys Ile Lys Asp Lys Ala Arg
```

```
              115                 120                 125
Asn Arg Tyr Phe Pro Ala Phe Glu Lys Val Leu Lys Ser His Gly Gln
            130                 135                 140

Asp Tyr Leu Val Gly Asn Arg Leu Ser Arg Ala Asp Val Tyr Leu Val
145                 150                 155                 160

Gln Val Leu Tyr His Val Glu Glu Leu Asp Pro Ser Ala Leu Ala Asn
                165                 170                 175

Phe Pro Leu Leu Lys Ala Leu Arg Thr Arg Val Ser Asn Leu Pro Thr
            180                 185                 190

Val Lys Lys Phe Leu Gln Pro Gly Ser Gln Arg Lys Pro Leu Glu Asp
                195                 200                 205

Glu Lys Cys Val Glu Ser Ala Val Lys Ile Phe Ser
            210                 215                 220
```

(2) INFORMATION FOR SEQ ID NO:32:

(i) SEQUENCE CHARACTERISTICS:
        (A) LENGTH: 221 amino acids
        (B) TYPE: amino acid
        (D) TOPOLOGY: linear (ii) MOLECULE TYPE: protein (xi) SEQUENCE DESCRIPTION: SEQ ID NO:32:

```
Ala Glu Lys Pro Lys Leu His Tyr Phe His Ala Arg Gly Arg Met Glu
1               5                   10                  15

Ser Thr Arg Trp Leu Leu Ala Ala Gly Val Glu Phe Glu Glu Lys
                20                  25                  30

Phe Ile Lys Ser Ala Glu Asp Leu Asp Lys Leu Arg Asn Asp Gly Tyr
            35                  40                  45

Leu Met Phe Gln Gln Val Pro Met Val Glu Ile Asp Gly Met Lys Leu
50                  55                  60

Val Gln Thr Arg Ala Ile Leu Asn Tyr Ile Ala Ser Lys Tyr Asn Leu
65                  70                  75                  80

Tyr Gly Lys Asp Ile Lys Glu Arg Ala Leu Ile Asp Met Tyr Ile Glu
                85                  90                  95

Gly Ile Ala Leu Asp Gly Glu Met Ile Leu Leu Leu Pro Val Cys Pro
            100                 105                 110

Pro Glu Glu Lys Asp Ala Lys Leu Ala Leu Ile Lys Glu Lys Ile Lys
            115                 120                 125

Asn Arg Tyr Phe Pro Ala Phe Glu Lys Val Leu Lys Ser His Gly Gln
            130                 135                 140

Asp Tyr Leu Val Gly Asn Lys Leu Ser Arg Ala Asp Ile His Leu Val
145                 150                 155                 160

Glu Leu Leu Tyr Tyr Val Glu Glu Leu Asp Ser Ser Leu Ile Ser Ser
                165                 170                 175

Phe Pro Leu Leu Lys Ala Leu Lys Thr Arg Ile Ser Asn Leu Pro Thr
            180                 185                 190

Pro Lys Lys Phe Leu Gln Pro Gly Ser Pro Arg Lys Pro Pro Met Asp
                195                 200                 205

Glu Lys Ser Leu Glu Glu Ala Arg Lys Ile Phe Arg Phe
            210                 215                 220
```

(2) INFORMATION FOR SEQ ID NO:33:

(i) SEQUENCE CHARACTERISTICS:
        (A) LENGTH: 217 amino acids (B) TYPE: amino acid
          (D) TOPOLOGY: linear (ii) MOLECULE TYPE: protein (xi) SEQUENCE DESCRIPTION: SEQ ID NO:33:

Pro Met Ile Leu Gly Tyr Trp Asn Val Arg Gly Leu Thr His Pro Ile
 1               5                  10                  15

Arg Leu Leu Leu Glu Tyr Thr Asp Ser Ser Tyr Glu Glu Lys Arg Tyr
                 20                  25                  30

Ala Met Gly Asp Ala Pro Asp Tyr Asp Arg Ser Gln Trp Leu Asn Glu
             35                  40                  45

Lys Phe Lys Leu Gly Leu Asp Phe Pro Asn Leu Pro Tyr Leu Ile Asp
 50                  55                  60

Gly Ser Arg Lys Ile Thr Gln Ser Asn Ala Ile Met Arg Tyr Leu Ala
 65                  70                  75                  80

Arg Lys His His Leu Cys Gly Glu Thr Glu Glu Glu Arg Ile Arg Ala
                 85                  90                  95

Asp Ile Val Glu Asn Gln Val Met Asp Asn Arg Met Gln Leu Ile Met
                100                 105                 110

Leu Cys Tyr Asn Pro Asp Phe Glu Lys Gln Lys Pro Glu Phe Leu Lys
            115                 120                 125

Thr Ile Pro Glu Lys Met Lys Leu Tyr Ser Glu Phe Leu Gly Lys Arg
130                 135                 140

Pro Trp Phe Ala Gly Asp Lys Val Thr Tyr Val Asp Phe Leu Ala Tyr
145                 150                 155                 160

Asp Ile Leu Asp Gln Tyr His Ile Phe Glu Pro Lys Cys Leu Asp Ala
                165                 170                 175

Phe Pro Asn Leu Lys Asp Phe Leu Ala Arg Phe Glu Gly Leu Lys Lys
                180                 185                 190

Ile Ser Ala Tyr Met Asn Cys Ser Arg Tyr Leu Ser Thr Pro Ile Phe
            195                 200                 205

Ser Lys Leu Ala Gln Trp Ser Asn Lys
    210                 215

(2) INFORMATION FOR SEQ ID NO:34:

(i) SEQUENCE CHARACTERISTICS:
          (A) LENGTH: 210 amino acids
          (B) TYPE: amino acid
          (D) TOPOLOGY: linear (ii) MOLECULE TYPE: protein (xi) SEQUENCE DESCRIPTION: SEQ ID NO:34:

Ala Pro Tyr Thr Val Val Tyr Phe Pro Val Arg Gly Arg Cys Ala Ala
 1               5                  10                  15

Leu Arg Met Leu Leu Ala Asp Gln Gly Gln Ser Trp Lys Glu Glu Val
                 20                  25                  30

Val Thr Val Glu Thr Trp Gln Glu Gly Ser Leu Lys Ala Ser Cys Leu
             35                  40                  45

Tyr Gly Gln Leu Pro Lys Phe Gln Asp Gly Asp Leu Thr Leu Tyr Gln
 50                  55                  60

Ser Asn Thr Ile Leu Arg His Leu Gly Arg Thr Leu Gly Leu Tyr Gly
 65                  70                  75                  80

Lys Asp Gln Gln Glu Gln Ala Ala Leu Val Asp Met Val Asn Asp Gly
                 85                  90                  95

-continued

```
Val Glu Asp Leu Arg Cys Lys Tyr Ile Ser Leu Ile Tyr Thr Asn Tyr
            100             105             110

Glu Ala Gly Lys Asp Asp Tyr Val Lys Ala Leu Pro Gly Gln Leu Lys
            115             120             125

Pro Phe Glu Thr Leu Leu Ser Gln Asn Gln Gly Gly Lys Thr Phe Ile
            130             135             140

Val Gly Asp Gln Ile Ser Phe Ala Asp Tyr Asn Leu Leu Asp Leu Leu
145                 150             155                 160

Leu Ile His Glu Val Leu Ala Pro Gly Cys Leu Asp Ala Phe Pro Leu
                165             170             175

Leu Ser Ala Tyr Val Gly Arg Leu Ser Ala Arg Pro Lys Leu Lys Ala
            180             185             190

Phe Leu Ala Ser Pro Glu Tyr Val Asn Leu Pro Ile Asn Gly Asn Gly
            195             200             205

Lys Gln
    210
```

GLUTATHIONE S-TRANSFERASE ISOFORMS

STATEMENT REGARDING FEDERALLY-SPONSORED RESEARCH

This invention was made with United States Government support awarded by NIH Grant #CA22484. The United States Government has certain rights in this invention.

FIELD OF THE INVENTION

The present invention relates to the creation of modified and mutant genes and isoforms of the enzyme class known as glutathione S-transferase and relates, in particular, to modified glutathione S-transferase genes for enzymes having particular utility for the detoxification of chemotherapeutic agents and cells transformed with such genes.

BACKGROUND OF THE INVENTION

Glutathione is a cellular tripeptide (γ-glutamylcysteinylglycine) which is perhaps the most abundant amino acid derivative contained in the cells of higher life forms. The middle amino acid in glutathione, cysteine, has a free thiol group which can compete with the nucleophilic site on nucleotide bases for reaction with electrophiles. Within the cell, glutathione functions so as to conjugate to xenobiotic toxic molecules in general, and electrophiles in particular, to render the toxic molecules less reactive against cellular macromolecules and to target the toxic molecules for subsequent metabolic and excretion pathways. The reactivity of glutathione to electrophilic molecules is facilitated by the enzyme glutathione S-transferase.

The glutathione S-transferase family of enzymes are thus responsible for the detoxification of a broad class of electrophiles and alkylating chemical agents. The glutathione S-transferase (GST) enzymes catalyze the conjugation of glutathione to a variety of compounds to create the products which are less reactive, more hydrophilic, and thus more easily excreted from the cells. The cytosolic glutathione S-transferase are known to belong to four classes, designated Alpha, Mu, Pi and Theta. A fifth class of glutathione S-transferases is a microsomal enzyme found primarily in liver endoplasmic reticulum. Higher cells each contain a family of many isozymes in each class with broad, yet overlapping, specificity. The enzyme family is believed to be one of the most important in the detoxification of reactive electrophiles within living cells.

Much recent effort has been focused on the elucidation of the tertiary structure of glutathione S-transferase so as to identify the active sites of the enzymatic molecule. It is known that the molecule binds quite specifically and with high affinity to glutathione, but binds promiscuously to a wide variety of xenobiotic, electrophilic, and alkylating chemical agents. Each of the enzymes of the four main cytosolic classes is found in dimeric form with two active sites per dimer each of which functions independently of the other. The active site has been characterized as consisting of a glutathione binding region (designated the G-site) and a non-specific hydrophobic binding region (designated the H-site) to accommodate the electrophilic substances.

The mechanism by which the enzyme enhances the nucleophilic reactivity of glutathione is poorly understood. Mechanisms have been proposed as to how that binding might occur, but the exact mechanism of enzymatic activity on the two substrates is, at this time, obscure. Similarly, while the binding specificity and the binding region to glutathione have been relatively well characterized, the nature, characteristics and binding specificity to the electrophile are less well understood.

One of the class of electrophilic compounds that are substrates for the glutathione S-transferase enzymes is the group of alkylating agents used in antineoplastic therapy. A common problem that is observed in modern cancer chemotherapy is the appearance of chemotherapeutic resistant tumor cells that, because of the resistivity, no longer respond appropriately to the antineoplastic agents. This resistance is often observed with many drugs that have no physical or mechanistic similarities to the original agent. The phenomenon, referred to as multi-drug resistance, has complicated attempts at cancer therapy. One common origin for the problem appears to be an increase in the expression of p-glycoprotein, a membrane protein pump which excretes large hydrophobic and toxic compounds from the cell. It has been demonstrated, in at least one instance, that a resistant population of malignant cells was shown to have a modified pattern of total glutathione S-transferase activity. A resistant population of MCF-7 breast cancer cells, identified through selection in adriamycin by Batist et al., *J. Biol. Chem.*, 261:15544–15549 (1986) resulted in a subset of cells which were approximately 200 fold more resistant than the parental cells. The resistant cells were found to exhibit a 45 fold increase in total glutathione S-transferase activity, the increase being due to the result of an appearance of an isozyme not expressed in the parental cell line. Previous experiments have demonstrated that an increase in glutathione S-transferase alone, an increase conditioned by the transformation of susceptible cells with a foreign DNA construct expressing the wild-type glutathione S-transferase coding region, could increase the resistance of cells to an antineoplastic agent. As reported in Puchalski and Fahl, *Proc. Natl. Acad. Sci. USA*, 87:2443–2447 (1990), expression of the rat 1-1, 3-3 and the human P1-1 isozymes of glutathione S-transferase in COS cells increased their resistance to the agent. The cells were then incubated with monochlorobimane, a compound that fluorescens upon conjugation with glutathione. Fluorescence cell sorting was used to isolate populations of cells that expressed the recombinant glutathione S-transferase, and that expression was shown to confer significant resistance to alkylating agents.

A problem in the use of glutathione S-transferase as a potential genetic transformation agent to imbue cells with resistance to antineoplastic or alkylating agents is the relatively non-specific targeting of the glutathione S-transferase enzyme to the electrophilic substrate. In view of the lack of data and lack of characterization as to the binding affinity and parameters of glutathione S-transferase to the electrophilic substrates, it was not known if modifications to the molecule could be made which might enhance or alter the binding specificity or reactivity of glutathione S-transferase to xenobiotic or antineoplastic agents.

SUMMARY OF THE INVENTION

The present invention is summarized in that modified mutant forms of glutathione S-transferase are created which have enhanced ability to react with a specific antineoplastic electrophilic or alkylating agents. Genes encoding such modified or mutant glutathione S-transferase agents may be selectively delivered into targeted cells to enhance the resistivity of those cells to the alkylating or neoplastic agents.

The present invention is also summarized in that a method is described for the creation of novel isoforms of glutathione S-transferase which have the novel desired activity against specific agents. The method is based on random mutation and selection with the selection being performed with the agent against which enhanced activity is sought. The mutation is preferably site directed to the amino acids associated with the H-site on the enzyme, so as to favor the creation of new, useful isoforms of the enzyme. The genes for the isoforms which confer enhanced resistance to the agent can then be transfected into other cells, to enhance the resistance of those cells to the agent as well.

It is an object of the present invention to provide a tool for possible gene therapy by enabling a class of novel isoforms of the glutathione S-transferase enzyme and a method to create such novel isoforms against a desired antineoplastic agent.

It is another object of the present invention to define DNA constructs which can be transferred into mammalian cells to confer upon the cells a novel trait of resistance to an antineoplastic agent.

It is yet another aspect of the present invention that the genetic construct expressing the glutathione S-transferase enzyme also conditions translocation of the expressed enzyme to the nucleus of the cell to facilitate protection of the nuclear genetic material of the cell.

Other objects, advantages and features of the present invention will become apparent from the following specification taken in conjunction with the accompanying drawings.

BRIEF DESCRIPTION OF THE DRAWINGS

FIG. 2 illustrates in schematic fashion how novel glutathione S-transferase genes might be used in cancer therapy.

FIG. 3 is an amino acid alignment of homologous GST sequences Rat GST 2-2 (SEQ ID NO:31); Human GST A1-1 (SEQ ID NO:32); Rat GST 3-3 (SEQ ID NO:33); and Human GST P1-1 (SEQ ID NO:34).

FIG. 5 is a sequence comparison of the gene for wild-type rat liver 2-2 glutathione S-transferase compared to the mutant genes created through method of the present invention. These sequences are set forth herein as SEQ ID Nos: 1–20 (odd-numbered are nucleic acid sequences; even-numbered are deduced amino acid sequences.

DETAILED DESCRIPTION OF THE INVENTION

Figure 1:
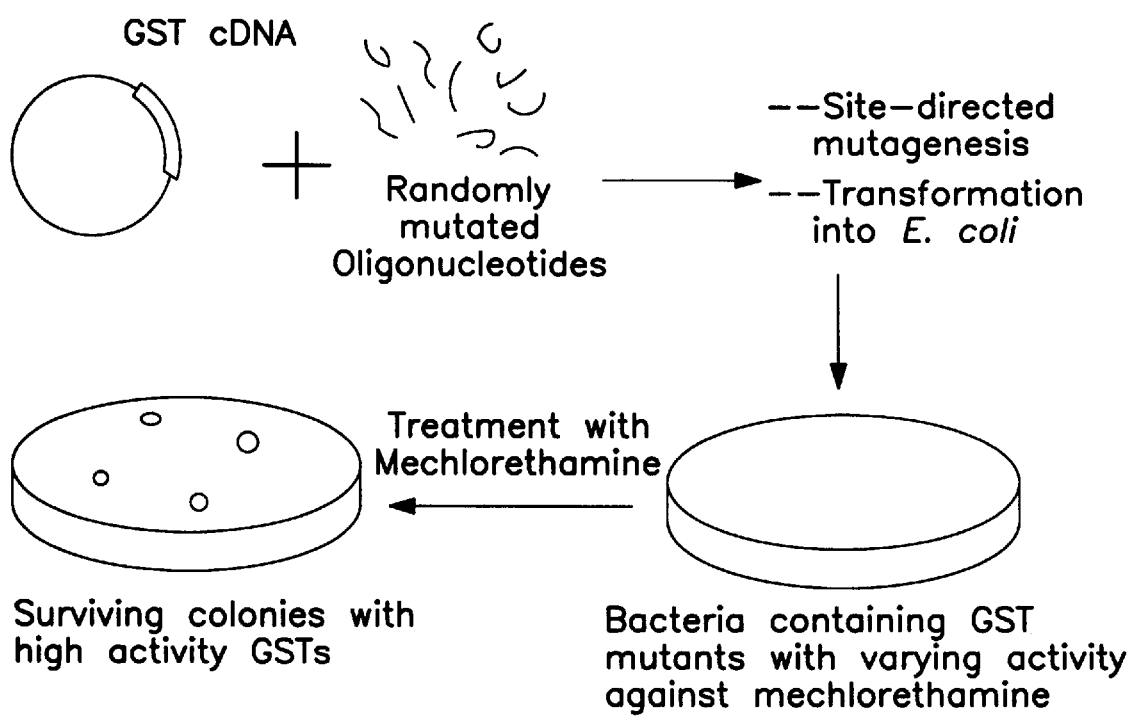
FIG. 1 illustrates in schematic fashion the mutagenesis and selection strategy in *E. coli* used in accordance with the present invention.

The present invention is generally directed toward the creation of engineered glutathione S-transferase (GST) enzymes which have novel substrate specificities or novel levels of activity in vivo. These enzymes, and the genes encoding them, are "engineered," in the sense that they are artificially and specifically altered from wild-type and native glutathione S-transferase enzymes and genes so that the expressed enzyme isoform is more effective in vivo in reacting with a toxic substance, such as an antineoplastic agent. The engineering can be, as described below, by site-directed random mutagenesis, or specific nucleotide or amino acid sequence modification, or can be, as also described below, achieved through random mutagenesis and selection for specific enzymatic activity. The engineering of the enzyme can involve alteration of substrate specificity so as to choose for enzymatic isoforms which have higher affinity for particular substrates or can involve other improvements or modifications to enzymatic function, such as changes in kinetic efficiency, proteolytic susceptibility, or level of enzyme gene expression, so as to result in an effectively increased level in cells into which genes for the engineered enzymes are expressed. The engineered glutathione S-transferase enzymes, and the genes which encode them, are useful since they confer resistance to antineoplastic agents and other toxic compounds on cells into which they are transformed. Such enzymes are therefore useful for gene therapy in which heightened resistance to antineoplastic agents or other toxic substances is required in certain categories of cells which can be genetically altered so as to enhance their resistance.

It is demonstrated for the first time by the data presented below that the in vivo effect of glutathione S-transferase activity can be substantially modified by engineering of the glutathione S-transferase enzyme isoform characteristics of transgenic cells. This adds a new tool to be used in increasing the resistance of cells to anticancer drugs. It now becomes possible to create genes for engineered glutathione S-transferase enzymes, to introduce those cells into selected non-malignant cells in the human body which might otherwise be vulnerable to toxicity from antineoplastic agents directed against malignant cells and, in that manner, imbue the healthy cells with a resistance to agents which will act against the targeted malignancy. It is a current limitation on the clinical delivery of many antineoplastic agents, such as agents of the nitrogen mustard family, that bone marrow progenitor cells are sensitive to the toxic effects of the agents. Depletion of bone marrow cells not only limits dosages of the agents but also increases clinical risk to the patient in general. A strategy to imbue bone marrow progenitor cells with resistance to such agents might then both allow for increases in dosage to alleviate the neoplasm and also increase the overall health of the chemotherapy patient.

Illustrated in FIG. 2, in schematic fashion, is how genes for the mutant forms of glutathione S-transferase (GST) might be used in cancer therapy. Prior to chemotherapy, a quantity of hematopoietic stem cells are removed from the patient. The cells are then transfected with an expression cassette for a mutant GST isoform which confers heightened resistance to the antineoplastic agent or agents prescribed for the patient. After transformation, the cells are returned to the patient who is then better able to withstand the toxicity of the agents. This strategy is, therefore, dependent on the efficacy of the mutant GST isoforms. The methods described here are directed to creating such mutant isoforms.

As discussed above, glutathione S-transferase enzyme facilitates the action of glutathione in its function of achieving a thiol-linkage to electrophilic molecules in the cell. To catalyze this reaction, the GST enzyme must bind to both substrates, and therefore the tertiary structure of the enzyme includes separate domains which bind to glutathione and the electrophilic target respectively. The enzyme has a tight binding site for glutathione, referred to as the G-site, and a discontinuous set of residues which assist in forming the relatively weak affinity for the electrophilic molecule to which the glutathione will be attached, those residues being jointly referred to as the H-site. All residues that are implicated in forming the H-site of a glutathione S-transferase enzyme are potential targets for gene engineering as described herein. It has been found here that the H-site is malleable enough to withstand random mutations while retaining the ability to support the enzymatic reaction. It has also been found that it is convenient, and probably necessary, to select for advantageous mutations in vivo in cells of the type in which the mutant enzyme isoforms are to be expressed.

There is overlapping, yet distinct, substrate specificity for the different glutathione S-transferase isozymes. This suggests that there are particular determinants at the active site that specify which compounds will bind in the proper orientation for catalysis of conjugation with glutathione. Despite the fact that each isozyme shows preference for certain types of compounds, the active site is clearly flexible enough to accommodate a wide array of structurally diverse compounds. This fact suggests that the glutathione S-transferases are not optimized for binding to and catalyzing the reaction with any one specific substrate. It was this background information that motivated the decision to identify mutant enzymes that conferred more resistance against a single anti-cancer agent, such as mechlorethamine used in the example below. Minor changes at the active site might yield a conformation more appropriate for binding to this specific compound. Data from crystallography reports has indicated that there are three regions of amino acids that are involved in forming the H-site, that part of the active site that is involved in binding electrophiles or alkylating agents. These regions are described as follows.

The first group of H-site residues immediately follows the catalytically important tyrosine residue found within the first six to ten residues of the protein, This segment of the protein connects strand $\beta 1$ to $\alpha$ helix A (using the notation of Reinemer et al., 1992). Important residues included phenylalanine 8, proline 9, and valine 10. In the Alpha class (Sinning et la., 1993), this region extends onto $\alpha$ helix A, including residues 10 through 15. The second region contributing to the formation of the H-site cavity is the carboxyl end of the $\alpha$ helix D. This large helix is located in domain II, and donates several residues to form one wall of the xenobiotic binding pocket. Among the residues implicated are leucine 107, leucine 108, proline 10, and valine 111 in the human A1-1 isozyme, and tyrosine 108 in the P1-1. The third region is the carboxyl terminus of the protein. In the Pi class, glycine 203 has been proposed to play a role, while in the Alpha class, which is 11 amino acids longer than the Pi class glutathione S-transferase, an $\alpha$ helix is formed, one face of which donates methionine 208, leucine 213, alanine 216, phenylalanine 220, and phenylalanine 222 to the H-site.

Armstrong, Gilliland, and colleagues investigated the structure of the rat Mu class enzymes with a particular interest in the catalytic reaction mechanism. They published the structure of the rat glutathione S-transferase 3-3 isozyme co-crystallized with two reaction products, as well as with an analog of a reaction intermediate. Investigation of this crystal defined the H-site for Mu class glutathione S-transferases as a pocket formed by tyrosine 6, tryptophan 7, valine 9, leucine 12, isoleucine 111, tyrosine 115, phenylalanine 208, and serine 209 (Ji et al., 1993, 1994). The side chains of tyrosine 6 and tyrosine 115 were also shown to provide more than hydrophobic contacts, as each formed hydrogen bonds with the o-nitro groups of the intermediate.

These studies defined regions for us to begin the search for mutants with altered catalytic properties. The rat glutathione S-transferase 2-2 isozyme sequence was aligned with the sequences of the three crystallized enzymes as shown in FIG. 3 The residues in the GST 2-2 sequence that corresponded to those residues involved in H-site formation for other GST isozymes were identified. Oligonucleotides containing a random mix of nucleotides at the H-site codons were designed. Oligonucleotide-mediated mutagenesis was performed allowing the generation of a population of mutant cDNAs that encoded GSTs with slightly altered catalytic properties. These mutants were expressed in bacteria that were subsequently treated with mechlorethamine, an anticancer agent of the nitrogen mustard family. After repeated rounds of treatment with the drug, bacteria were grown as individual colonies. The plasmid DNA was recovered and sequenced to identify the mutants in the H-site regions.

Mutations were identified at the codon 9–11 region of the protein. These mutant enzymes survived presumably because they were better able to protect a cell from the drug. The fact that the mutant enzyme was responsible was proved by expressing the mutant enzymes in new bacteria that had not previously been exposed to the drug. The mutant enzymes conferred as much as 7-fold resistance to the nitrogen mustard compound (i.e., it took 7 times more drug to kill as an equal number of bacteria containing the mutant proteins compared to wild-type bacteria). The wild-type GST sequence conferred only 1.7-fold resistance.

Thus, through these experiments in bacteria, mutant enzymes were identified that exhibit a four-fold improvement in protection against this alkylating agent, when compared to the wild-type enzyme. We believe that this work sets the stage for more experiments in which the populations of catalytically varied glutathione S-transferase enzymes are expressed in mammalian cells and selected with alkylating agents such as mechlorethamine and melphalan. Sequences of the protein that we will target are the three regions described above that contribute to formation of the H-site, namely:

Codons 9–11 of the rat glutathione S-transferase 2-2 isozyme. These residues form one wall of the H-site.

Codons 108–110 of the rat glutathione S-transferase 2-2 isozyme. These residues, which lie at the carboxyl terminus of alpha helix D, also contribute hydrophobic sidechains to that H-site.

Codons 210–220 which forms an alpha helix at the carboxyl end of the protein.

Other glutathione S-transferase isoforms of all four cytosolic classes, both from humans and from other organisms have been found to vary in their exact sequence and location of their respective H-sites. However, for all known glutathione S-transferase sequences, there is a tyrosine at about position 6 and homologous sequences corresponding to amino acids 108–110 and 210–220 of this rat 2-2 isozyme sequence. For any new glutathione S-transferase isozyme sequence, available sequence watching and alignment software can be used to perform sequence alignment to locate the corresponding H-sites in the new isozyme sequence. It is specifically envisioned that the H-sites of other such isoforms can be manipulated in the same manner as the isoforms which have been manipulated here.

The methodologies used to create altered or mutant forms of glutathione S-transferase useful within the present invention range from the intelligently selected alteration of specific nucleotides or amino acids to the random mutageneses by any of a variety of techniques of the targeted areas of the protein. It is, however, preferred for purposes of efficiency that the mutagenesis be site-directed at the H-site to most rapidly develop isoforms having the desired altered characteristics.

To demonstrate that the technique of the present invention can result in altered glutathione S-transferase enzymes which have the effect of conferring resistance in vivo in selected cells, a site directed mutagenesis and selection technique was conducted in the bacterial system E. coli with resistance conferred to the antineoplastic agent mechlorethamine. This procedure is illustrated schematically in FIG. 1. As described in detail in the examples below, it was possible, by mutation and selection, to create altered glutathione S-transferase 2-2 activity, expressed in the bacteria, to create pools of mutant bacteria which had a 4 to 7 fold increase in resistance to mechlorethamine as compared to wild-type glutathione S-transferase bacteria. The increase in resistance is primarily due to an elevation of the steady state levels of the mutant enzyme contained within the bacteria as compared to the amount of enzyme contained in wild-type bacteria. The mutations were also found to effect the catalytic activity of the enzyme itself. This result was conducted not because bacteria resistant to mechlorethamine are themselves the object of the present invention. Rather, the experiment was undertaken to demonstrate that modified glutathione S-transferase enzymes can be created by random mutagenesis and selection which confer upon their host cells a heightened resistance to antineoplastic agents.

In conducting the random mutagenesis experiments described in the examples below, rather than simply mutating native sequences for the glutathione S-transferase activity, it was decided to generate a large population of randomly mutated glutathione S-transferase cDNAs by the use of oligonucleotides that were mutated in the specific regions of the cDNA implicated in the H-site.

In an in vivo mutagenesis selection protocol, as envisioned here, the activity of the randomly mutagenized isoforms are tested empirically by challenging host cells transformed with random gene constructs with the agent against which resistance is sought. The specific mechanism by which the enhanced level of activity against the target agent is achieved is not critical. The novel isoform can be more effective because of enhanced specificity to the target agent molecule, because of enhanced catalytic kinetics, because of higher level of expression in the host cells, or simply because of longer half-life in the host cells due to protease resistance. Whatever the mechanism of action, the gene for the mutant enzyme will, by definition, confer upon cells in which it is transformed an enhanced level of practical resistance to the targeted agent. Once a colony of cells which has enhanced resistance to the targeted antineoplastic agent has been identified, the gene encoding the glutathione S-transferase activity can be recovered from the surviving cells. That same mutant gene can then be replicated and transformed or transfected into other wild type cells to confer upon those cells the trait of resistance to the agent. Techniques are well known to recover, characterize, and replicate, coding sequences and genes for specific enzymes. Using the preferred method of site-directed mutagenesis, the mutant genes can be recovered from any type of cell by PCR reaction using primers located at extreme ends of the inserted randomized genes. Once the mutant genes are recovered, they can be assembled into expression cassettes or vectors for the desired host cell type. Such vectors, many of which are known and commercially available, include flanking regulatory DNA sequences to express any protein coding sequence in selected hosts. Techniques for inserting such expression vectors into host cells are also well known. For mammalian cells, suitable transfection methods include retroviral delivery, electroporation, liposome encapsulation and particle mediated gene delivery. The method of gene delivery is now known to be irrelevant to the expression of the inserted transgene.

While the example below demonstrates the fact that mutant isoforms of glutathione S-transferase can be created which have heightened levels of activity in vivo, it is envisioned that new mutant isoforms will be created to be effective in mammalian cells in general and in bone marrow cells in particular. Because the activity of an enzyme is dependent on a large number of environmental conditions, it is specifically envisioned that the site directed mutagenesis and selection techniques described here will be conducted in mammalian cells to create mutant glutathione S-transferase isozymes having enhanced activity to specific antineoplastic agents under mammalian cytosolic conditions. Once such mutant isozymes are created, the genes for those isozymes can be recovered and inserted into expression vectors for delivery into targeted cells of a patient. In considering this protocol, several possible enhancements or derivatives to enzyme and its expression cassette for clinical use are envisioned. These will now be described.

One area for additional improvement to in vivo efficacy of the glutathione S-transferase enzyme is protein stability. The level of an expressed protein in a heterologous eukaryotic host cell is tightly regulated by the non-lysosomal protein degradation system. While many of these proteins are sorted for rapid degradation, few are observed to remain stable with long half-lives. One of the generalizations to emerge from many investigations is that the longevity of a protein in eukaryotic cells is mainly influenced by its exterior architecture, and sorting for selective degradation of proteins is mainly specified by portions of its amino acid sequences constituting signals to be recognized by the enzymes of protein degradation. For example, some proteins contain stretches of certain amino acids (PEST sequences; Proline, Glutamic acid, Serine, Threonine) flanked by clusters of positively charged amino acids which compose a signal for rapid degradation of the proteins. The second essential component of the degradation signal depends on the nature of the N-terminal residue (penultimate to the initiator Met). In eukaryotes, the presence of a destabilizing residue (F, L, W, Y, R, K, H, I, N, Q, D, E) at the N-terminus makes the protein unstable when compared to the stabilizing residues (V, P, M).

The process of selective intracellular degradation in eukaryotes is carried out by the ubiquitin-mediated pathway. Specific lysine residues present within the "destruction boxes" are recognized and covalently modified by the low molecular weight peptide ubiquitin which initiates the process of protein degradation by an ATP-dependent protease. Modification of these signals to prevent protein degradation has been successfully used in several cases, and we intend to use similar protocols for engineering stable GSTs. Amino terminal lysines at positions 3, 35, and 63 may be relevant for directing the GSTs to this pathway, and we will conservatively change them.

In earlier work from our lab, in order to prolong the longevity of a GST in mammalian cells, we redesigned the N-terminus if the GST by replacing the destabilizing amino acid residues with those known to impart greater stability. We made a fusion protein comprised of the 19 N-terminus amino acid residues of β-galactosidase fused to the amino end of GST, and the chimeric protein was found to be highly stable. This modification, aimed at conferring greater stability to the GST had no diverse effect on its catalytic properties.

Based upon these earlier studies, we will systematically alter N-terminal amino acids as well as exterior lysine residues to diminish GST degradation, and thus, increase the abundance of the recombinant GSTs in the host mammalian cells.

Another strategy to enhance glutathione S-transferase efficacy in vivo is to direct localization of the expressed enzyme to the nucleus. It is envisioned that the structure of the wild-type, 221 amino acid GST 2-2 molecule may be modified by adding a nuclear-localizing sequence to now enable entry of the structurally-modified protein into the nuclear compartment of mammalian cells. The competing reactions between covalent modification of nuclear DNA by an alkylating drug or conjugation of the drug to glutathione catalyzed by a GST are at the heart of this proposed goal. Previously, recombinant GST expression vectors were constructed that enabled us to express the GST only within the cytosolic compartment of transfected cells. The location of the expressed enzyme was determined by both in situ immunostaining of COS cells for the recombinant GST, as well as by western immunoblot analysis of proteins from cytosolic and nuclear fractions of cells transfected with a wild-type GST expression vector Though cells which received and expressed recombinant, wild-type GSTs did acquire resistance to alkylating drugs in our previous experiments (Puchalski and Fahl, Proc Natl. Acad. Sci. USA 87:2443–2447, 1990), the possibility remained that greater protection could be achieved by also conjugating those drug molecules that directly accessed the nuclear compartment by diffusion across the cell's plasma membrane and then diffusing across the immediately apposed nuclear membrane without being exposed to any of the recombinant GST which had been localized within the cytosolic compartment. The immediate apposition of these two membranes enables hydrophobic, highly-reactive drug molecules to diffuse freely across these two membranes and freely access nuclear DNA. Our goal in this alternative, is to now introduce the drug-detoxifying ability of a wild-type or efficient mutant GST into the nuclear compartment of the cell, and by increasing the number o drug binding sites that are available on GST molecules within the nuclear compartment, kinetically favor GST conjugation of the drug rather than alkylation of DNA bases.

In experiments already completed in our lab, we first designed and constructed a recombinant expression vector that had adjacent KpnI and NheI restriction sites immediately 3' to the ATG initiation of translation codon. These sites were engineered into the vector to enable simple, cassette substitutions of different nuclear localizing sequences into the KpnI site, and simple cassette substitutions of different GST sequences into the NheI and XhoI sites, while still maintaining the appropriate reading frame relative to the above-cited ATG initiation codon. SEQ ID NO: 21 sets forth the DNA sequence for one construct, where a DNA fragment encoding a 37 amino acid nuclear localizing domain from the rat glucocorticoid receptor (Picard and Yamamoto, EMBO Journal 6:3333–3340, 1987) was fused to the amino terminus of the GST 2-2 sequence. A preliminary experiment from our lab, in which this construct was transfected into COS monkey cells, indicated that the recombinant protein was now discernibly larger than the cytosolic GST 202, and that it could now also be detected in the nuclear compartment of these COS cells, whereas the cytosolic GST 2-2 could not be. The DNA sequence for a second nuclear GST construct is set forth in SEQ ID NO: 22. Here we have taken the 7 amino acid nuclear localizing signal from SV40 T antigen and fused it to the amino terminus of the GST 2-2 protein. The localizing efficiency of both of these recombinant gene products will be compared as well as the kinetic efficiency of these two GST catalysts, and the more effective nuclear leader will be carried forward for subsequent applications.

In this enhancement alternative, it is proposed to modify the normally soluble, cytosolic GST to enable it to localize to, and anchor in, the inner surface of the mammalian cell plasma membrane. The membrane defines the outer limits of a cell; it is through this lipid bilayer that all substances must pass to enter the cell. The reasons to believe that a membrane-bound GST would be more protective to a cell are two-fold:

1) First, localization of the GST detoxification enzyme to the membrane may have the effect of conjugating the alkylating drug to glutathione as it enters the cell. This is a "trap it early" strategy.

2) A second reason for hypothesizing that this may be an effective approach is that most alkylating agents that serve as substrates for GSTs are hydrophobic compounds. Thus, the drugs may partition to the membrane environment of the cell, and therefore may be at higher concentrations in the outer vicinity of the plasma membrane. Expressing GSTs in this region may be useful for metabolizing these alkylating drugs.

The strategy that we will follow to generate this modified enzyme will be to synthesize a GST now containing a 17 amino acid farnesylation domain at the carboxy terminus; this 17 residue domain will be identical to the farnesylation domain which is present as the carboxy terminal 17 residues of the K-RAS protein. This farnesylation domain consists of a CAAX box on the carboxy terminus (where C is cysteine, A is an aliphatic residue, and X is any amino acid) and an adjacent polybasic stretch of 6 lysine residues [Hancock et al., Cell 57:1167 (1989), Cell 63:133 (1990)]. It has been shown frequently that attachment of this sequence to the carboxy terminus of a protein directs that protein to the appropriate farnesylation enzymes within the cell and the subsequent catalyzed addition a lipid molecule to the GST and its subsequent insertion into the inner leaf of the plasma membrane (for a recent example, Stokoe et al., Science 264:1463–1467, 1994).

The following nucleotide sequence will be fused to the 3' end of the GST 2-2 cDNA:

```
AAA GAT GGT AAA AAG AAG AAA AAG AAG(SEQ ID NO:23)
K   D   G   K   K   K   K   K   K  (SEQ ID NO:24)

TCA AAG ACA AAG TGT GTA ATT ATG TAA
S   K   T   K   C   V   I   M-
                                stop
```

This sequence is sufficient to direct a protein to the inner leaf of the plasma membrane.

The above discussion contemplates a mutant GST expression cassette that achieves efficiency of enzyme activity by modifications to the enzyme sequence. Increases in activity can also be achieved by enhancements to other elements o the expression cassette. For example, it is envisioned that a specific regulatory element may be added to the recombinant promoter that will enable more efficient transcription of our recombinant GST gene to occur within the mammalian cells into which it is transfected. Transcription of the recombinant GST gene in mammalian host cells will be regulated by one of a few known viral promoters which are proven to express well in mammalian cells, including the CMV immediate-early promoter and the 5' long terminal repeat (ltr) promoter from Maloney leukemia virus. Although either of these promoters can be expected to maintain an efficient level of expression of mRNA encoded by the recombinant GST expression gene in our host cells, we propose to position an additional transcription regulatory element either within or immediately adjacent to the indicated promoter, in order to introduce the novel regulatory aspects associated with this element into the expression of our recombinant GSt gene. We will introduce a single 41 bp DNA sequence known as the Electrophile Responsive Element (EpRE, Friling et al., *Proc. Natl. Acad. Sci. USA,* 87:6258–6262 (1990), EPRE sequence=5'-TAGCTTGGAAATGACATTGCTAATGGT-GACAAAGCAACTTT (SEQ ID NO: 25)) or Antioxidant Responsive element into a site at −165 from the mRNA DCAP site of the CMVie promoter or Maloney 5' ltr promoter. Or, based upon previous example, we may introduce up to five concatamerized copies of this 41 pb EpRE sequence at −165 from the mRNA CAP site of the CMVie promoter or Maloney 5' ltr promoter in order to possibly get a more magnified transcription response upon exposure of cells to the electrophilic drug. By introducing this regulatory element into these promoter sites we will capitalize upon the capacity of this element to enhance transcription upon exposure of the cells to one or more known electrophilic chemicals, chemicals that include the alkylating, chemotherapeutic drugs that we hope to detoxify with the recombinant GSt that is served by this EpRE-containing promoter. To summarize, exposure of mammalian cells which carry our recombinant expression gene to any of a host of electrophilic, alkylating drugs would result in the activated transcription of the recombinant GST gene because of the EpRE element within or adjacent to the promoter resulting in heightened production of recombinant GST in direct response to the presence of the alkylating drug. In the absence of alkylating drug, transcription of the recombinant GSt gene would return to the basal level of transcription that is normally associated with the CMVie ro Maloney 5' ltr promoters. Previous studies from our laboratory, as well as from other laboratories, illustrate the activating transcriptional response which has been assigned to this 41 bp regulatory element upon exposure of cells to a host of different electrophiles, in this case hydrogen peroxide.

Although inclusion of the EpRE regulatory element within the recombinant promoter does not directly reflect a structural change to the GST protein, it does provide a novel mechanism by which we can significantly augment (up to 6–8 fold in our experiments, FIG. D) the level of recombinant GST in a mammalian cell host. As described previously in this application increased abundance alone of a recombinant GST in an *E. coli* cell can serve to confer significant resistance or protection against an alkylating drug.

It is envisioned that we will analyze the relative benefits of each single GST modification described previously, and then combine the useful ones into a single expression vector that will enable the concurrent production of one, two or three recombinant GSTs in a single cell, enzymes localized to the cytosol, nucleus and inner plasma membrane, respectively. Aside from the localizing sequences on these GSTs, we will of course use that GST molecule which contains those H-site alterations that we had previously shown to enable the enzyme to more efficiently detoxify alkylating nitrogen mustards. A previous report from our lab (Manoharan et al., *Molecular Pharmacology* 39:461–467 (1991)), describes a cloning strategy that enables the configuration of several prompter: cDNA expression cassettes on a single plasmid which allows maximal transcription of each expression cassette. Presently, there are no known reports of cellular toxicity associated with the production of GST; there is no evidence that is, or can become, a toxic protein to cells. Rather, in human and rodent hepatocytes, the combined expression of several GST isoforms accounts for 3–10% of the cytosolic protein. Likewise, the combined production of recombinant GST in all of these cell compartments will be provided an ample supply of the other substrate for the conjugation reaction, namely glutathione, as it is present at concentrations between 0.1–0.5 mM in all of the cellular compartments, including the nuclear compartment.

EXAMPLE 1

This example describes the creation of mutant glutathione S-transferase enzymes effective in *E. coli* to increase resistance to mechlorethamine. The example demonstrates that modification to the H-site of the enzyme are possible while retaining and increasing activity in vivo.

Plasmid Construction: the cDNA of rat class alpha glutathione S-transferase 2 was inserted in-frame into the pUC120 plasmid, described in Manoharan et al., *J. Biol. Chem.,* 267:18940–18945 (1992). The entire promoter-coding region cassette from this plasmid was then amplified using polymerase chain reaction with oligonucleotide primers containing additional EcoRI (5') and BamHI (3') sites. This DNA fragment was inserted into the multiple cloning site of a modified pAlter plasmid (Promega Corp., Madison Wis.). Because the pAlter plasmid contains the $P_{lac}$ promoter identical to the one in our promoter-cDNA cassette, the 213 bp HindIII-PvuII fragment containing the $P_{lac}$ promoter was then deleted. Deletion of the promoter was done to improve synthesis of the glutathione S-transferase protein product and prevent any RNA polymerase competition or interference that might arise. The modified plasmid was designated pAMG88. The 843 bp promoter-cDNA cassette was then inserted into the EcoRI and BamHI sites of the pAMG88 multiple cloning site. The resultant plasmid (pAMG207) was then tested for its ability to direct synthesis of the glutathione S-transferase 2-2 protein, and for high efficiency mutagenesis. Ampicillin-resistant plasmids (pAMG88a and pAMG207a) were also constructed by performing a mutagenesis reaction in the presence of the ampicillin repair oligonucleotide alone.

Mutagenesis. Two types of mutant oligonucleotides were used for random oligonucleotide-directed mutagenesis in this study. The first set contained completely random sequences at the targeted codons. The targeted codons were at the H-site of the enzyme, amino acid locations 9–14, and 108–112. The wild-type codons were replaced with NNS, where N represents an equal mixture of all four bases and S represents an equal mixture of G and C. These random oligonucleotides, as well as all standard oligonucleotides used in this study, were synthesized on an Applied Biosystems Model 391 PCR-mate EP DNA synthesizer. To assess the quality of the random oligonucleotides, mutagenesis was performed with oligonucleotides Yc(9–11)random and Yc(108–110)random. Over 15 mutant clones from each pool were sequenced to identify the mutations contained on the oligonucleotides. There was shown to be no nucleotide bias in either oligonucleotide. To determine if enzyme activity was retained in variants containing mutations at three H-sites residues, several clones from each pool were tested for glutathione S-transferase activity with the commonly used substrate 1-chloro-2,4-dinitrobenzene. While the mutants at residues 9–11 generally had more activity than enzymes mutated in residues 108–110, several clones from each pool retained full activity. This demonstrated that there were catalytically active variants in each pool of randomly mutated enzymes.

The second set of oligonucleotides was synthesized with a small concentration of the three non-wild-type bases at each position in the targeted codons. These oligonucleotides, referred to as "spiked," were synthesized by Genosys Biotechnologies, Inc. (The Woodlands, Tex.). The oligonucleotide Yc(9–14)spike was synthesized with 90% wild-type and 10% mutant bases at six target codons, while the remaining spiked oligonucleotides were synthesized with a 5% contamination at eleven target codons. According to the binary distribution equation, these values maximized the fraction of oligonucleotides containing one or two mutations and minimized the frequency of wild-type (no mutation) oligonucleotides synthesized.

The following table illustrates the oligonucleotides used.

TABLE 1

Oligonucleotides used for random mutagenesis

| Oligonucleotide | Sequence | |
|---|---|---|
| Yc(9–11)random | CCT GGG AAG C-CA GTA CTT CAC-TAC NNS NNS NNS AGG GG-G AGA ATG GAG | (SEQ ID NO:26) |
| Yc(108–110)random | T CTG GAT GAA ATA GTA CAC CAT-NNS NNS NNS ATT C-CC CCT GGG GAG | SEQ ID NO:27 |
| Yc(9–14)spike | CCT GGG AAG C-CA GTA CTT CAC TAC TTC-GAT GGC AGG GG-G AGA ATG GAG CCC ATC CGG | (SEQ ID NO:28) |
| Yc(102–112)spike | CA GAA GGA GTG GCA GAT CTG GAT-GAA ATA GTA CTC CAT TAC-CCT TAC ATT C-CC CCT GGG GAG AAA G | (SEQ ID NO:29) |
| Yc(210–220)spike | G AGG AAG CCA CTC GAG GAT-GAG AAA TGT GTA GAA TCT G-CA GTT AAG ATC TTC AGT-TAA A GGATCC TCTAG | (SEQ ID NO:30) |

Cytotoxicity assays and enrichment for highly resistant mutants. Cultures of cells were grown in Luria Broth 20–25 hr to near saturation. Cells were diluted 1 to 10 in Luria Broth (LB), and grown for an additional 5 hr. Cells were diluted into M9 minimal media containing 2 mM isopropyl-β-D-thiogalactopyranoside (200 μl cells into 4 ml media) and induction continued for 12 hr to an $OD_{590}$ of ~1.4. Finally, we diluted the cells and treated with several concentrations of mechlorethamine dissolved in dimethylsulfoxide (total volume, 1 ml; solvent concentration, 2.5%). Cells were incubated three hr at 37° C. and then an appropriate volume of cells was plated. Plates were incubated at 37° C. until visible colonies appeared (~20 hours). Cytotoxicity curves represented the percent survival compared to solvent-treated cells at various drug concentrations.

To select for glutathione S-transferase enzymes that conferred increased resistance to mechlorethamine, a population of mutant plasmids was generated through the mutagenesis procedure using one of the random oligonucleotide pools and transformed into AG-1 competent *E. coli* (Stratagene, La Jolla, Calif.). Cells were grown for 5 hr in LB in the absence of antibiotic selection, and then for 17 hr under selection with both ampicillin and tetracycline. The cells were washed twice in media and induced for 12 hr. The bacteria were then treated for 3 hr with 20 μM mechlorethamine. After treatment, cells were removed from mechlorethamine-containing media by centrifugation, washed once, and resuspended in media for a second 12 hr protein induction. This cycle of enzyme induction and mechlorethamine treatment was continued for 6 rounds using increasing concentrations of the alkylating agent. The concentrations were used 20, 40, 150, 150, 350, and 500 μM. After the 500 μM treatment, cells were incubated in LB, and after 10 hr of growth, the surviving plasmids were obtained by standard miniprep procedures. These plasmids were transformed back into wild-type AG-1 bacteria and subjected to two more rounds of induction and treatment with 500 μM mechlorethamine. This was done to decrease the likelihood of host-mediated resistance factors affecting the selection of glutathione S-transferase containing plasmids.

Protein analysis. Western blots were performed as described by Gulick et al., *J. Biol. Chem.* 267:18946–18952 (1992) using the anti rat Ya/Yc (1-1/2-2) polyclonal antiserum generously provided by Dr. Cecil Pickett. The glutathione S-transferase 2-2 isozyme was purified essentially as described in Huskey et al., *Arch. Biochem. Biophys.* 279:116–121 (1990). Lysate were centrifuged at 2500 g for 20 min., then adsorbed to S-hexylglutathione agarose. As reported by Hayes in *Glutathione S-Transferases and Drug Resistance,* Taylor and Francis, London (1990), the glutathione S-transferase 2-2 isozyme was found to elute more efficiently with 5 mM S-hexylglutathione than with 5 mM glutathione.

Apparent inhibition constants for mechlorethamine were determined by measuring the ability of the compound to inhibit the glutathione S-transferase catalyzed reaction with cumene hydroperoxide. The assay was performed as described by Lawrence and Burk (34) except the preincubation was 2.5 min rather than 5 min, and the reaction was started with the addition of glutathione. The assays were performed in triplicate at each combination of concentrations. The glutathione concentration was held constant at 2 mM. Four concentrations of cumene hydroperoxide (ranging from 0.5–2 mM) and mechlorethamine (0–0.5 mM) were used. The inhibition was determined to be competitive against cumene hydroperoxide. The apparent kinetic constants were determined by non-linear curve fitting (SigmaPlot, Jandel Scientific, Corte Madera, Calif.) to the equation for competitive inhibition.

Wild-type glutathione S-transferase confers resistance to mechlorethamine. To maximize the efficiency of a system for identifying high resistance mutants, it was desirable to use a single plasmid that both directed bacterial synthesis of the glutathione S-transferase and allowed efficient oligonucleotide-mediated mutagenesis. A promoter-cDNA cassette was generated by inserting the glutathione S-transferase 2-2 cDNA in frame with the initiator codon of the pUC120 plasmid. To achieve a higher mutagenesis efficiency than was attainable with the pUC120 plasmid, the entire promoter and cDNA were then removed from this plasmid and inserted into the modified pAlter plasmid, as described above.

Using bacteria harboring these plasmids, we tested to see if the wild-type glutathione S-transferase 2-2 was able to confer resistance to mechlorethamine, a DNA-alkylating agent used primarily to treat Hodgkin's and other lymphomas. This compound undergoes spontaneous rearrangement to form an aziridinium ion that is capable of covalently binding to nucleophilic regions of DNA. To determine if expression of glutathione S-transferase would confer a selective advantage to mechlorethamine-treated cells, equal numbers of induced cells containing the glutathione S-transferase expression plasmid (pAMG207) were combined with induced cells containing the control plasmid (pAMG88). The mixtures of cells were then treated with solvent or mechlorethamine and plated. We then isolated plasmid DNA from the surviving cells and determined the number of glutathione S-transferase positive and negative clones. At three concentrations of mechlorethamine tested, a higher number of colonies expression glutathione S-transferase were obtained, as indicated in the following Table 2. This result indicated that wild-type glutathione S-transferase 2-2 conferred resistance to mechlorethamine in bacteria and suggested that it would be possible to select for any mutants that conferred additional resistance.

TABLE 2

Wild-type GST confers resistance to nitrogen mustard when expressed in *E. coli*

| [nitrogen mustard] | GST⁻ colonies | GST⁺ colonies | |
|---|---|---|---|
| 0 | 11 | 14 | |
| 5 μM | 7 | 20 | $p < 0.2$ |
| 50 μM | 4 | 24 | $p < 0.02$ |
| 500 μM | 3 | 24 | $p < 0.01$ |

Random Mutagenesis. To generate a large population of randomly mutated glutathione S-transferase 2-2 cDNAs, we used oligonucleotide that were mutated in regions of the cDNA that encode amino acids important for binding hydrophobic compounds. We targeted these regions of the active site because an increase in affinity towards mechlorethamine would be one way in which mutant enzymes could confer greater resistance than observed with the wild-type enzyme. An amino acid alignment shown in FIG. 3 illustrates the residues that have been implicated in forming the H-site by crystallography studies of three glutathione S-transferase enzymes. Included in the alignment is the sequence of the rat glutathione S-transferase 2-2, an isozyme that is important in resistance to nitrogen mustard compounds. Because the regions important for electrophile binding were clustered in three areas of the sequence of the enzyme, we were able to design several oligonucleotides that each spanned one of the three regions of the 2-2 isozyme sequence.

As described above, two different strategies were used to design the mutant oligonucleotides listed in Table 1. The first two oligonucleotides were designated random and contain the sequence NNS in place of the targeted codons. Each mutant, therefore, contained a random mix of amino acids at all three codons under investigation. In the second type of oligonucleotide, the targeted region was increased in length but the severity of mutagenesis was lowered. These spiked oligonucleotides were synthesized by contaminating the synthesis of each base of the targeted region with a mixture of the three non-wild-type bases.

Identification of mutant glutathione S-transferases that confer increased resistance to mechlorethamine. The mutant oligonucleotides were used as primers in mutagenesis reactions to generate a large population of mutant cDNAs in plasmid pAMG207. Bacteria harboring these plasmids were subjected to six rounds of enzyme induction and treatment with increasing concentrations of mechlorethamine. The plasmids from surviving bacteria were then isolated and transformed into wild-type bacteria for two more rounds of induction and treatment to reduce the likelihood that differences in endogenous sensitivity of individual bacterial cells would affect the outcome of the experiment. After the final mechlorethamine treatment, cells were plated on agar plates and plasmids from individual colonies were sequenced to determine the deduced amino acid sequence of the mutated regions. The amino acid sequences of the mutant enzymes are shown in the following Table 3.

TABLE 3

Amino acid sequence of surviving clones

| Mutant Clone | Codon 9 | 10 | 11 |
|---|---|---|---|
| Wild-type enzyme | Phe | Asp | Gly |
| 9-11s1 | Ala | Cys | Ile |
| 9-11s4 | Val | Cys | Ile |
| 9-11s7 | Met | Lys | Ile |
| 9-11s9 | Val | Arg | Ile |
| 9-11s15 | Gly | Ile | Leu |
| 9-11s16 | Val | Pro | Leu |
| 9-11s21 | Val | Ile | Cys |
| 9-11s22 | Cys | Asp | Ile |
| WCs3 | Leu | Asp | Gly |

The aligned nucleotide sequences of each of the above clones, and their corresponding amino acid sequences, are set forth in SEQ ID NOS: 3–20 below and in FIG. 5. In reviewing these sequence listings, it is important to note that the amino acid numbering convention of the investigators here, and used in this specification, does not count the N-terminal methionine, in contrast to the required sequence presentation format below, which does count that methionine. Hence, for example, the codons designated at position 9 above appear at position 10 in the formal SEQ IDs below.

Figure 4:
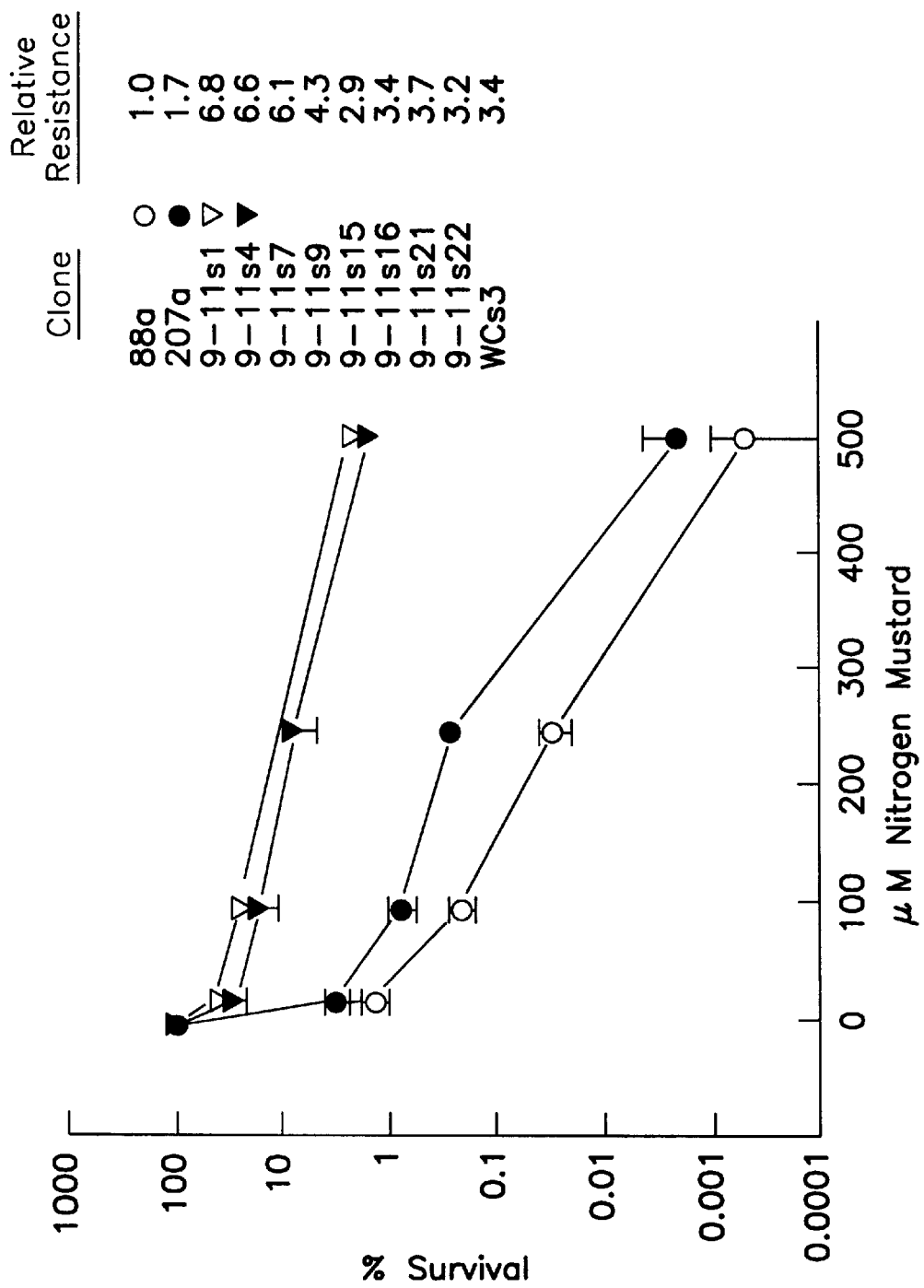
FIG. 4 is a graphical representation of results of an experiment described in Example 1 below.

It was then decided to test whether these selected sequences conferred more resistance to mechlorethamine than observed with the wild-type enzyme. Clones of cells containing the different plasmids were induced for 12 hr and then treated with varying concentrations of mechlorethamine. All of the mutants conferred more resistance than the wild-type enzyme did, and the two best mutants conferred up to four times the resistance against this alkylating agent than the original wild-type glutathione S-transferase 2-2. Shown in FIG. 4 is graphical representation of the results of survival tests of the two best mutants. To confirm that this was a result of the three mutations at codons nine through eleven identified, we reconstructed one of the mutants. An oligonucleotide was designed that generated an identical mutation as that seen in clone 9–11s1, namely alanine, lysine, and isoleucine at codons nine through eleven. This mutant enzyme, when expressed in bacteria, conferred the same degree of increased resistance, as that observed with the selected mutant 9–11s1, confirming that the resistant phenotype was a result of the three codon mutation that we identified.

Analysis of Mutant Enzymes. The mutant enzymes were studied to test the steady state levels of protein present in a cell. Lysates of induced bacterial cultures were made for each of the clones, and an equal amount of protein was loaded on a polyacrylamide gel. Western Blot analysis showed the amount of recombinant glutathione S-transferase present for the different clones. All of the mutant proteins were expressed to higher steady state levels than the wild-type enzyme. There was not, however, a simple one-to-one correlation between the amount of enzyme present, and the amount of resistance conferred, suggesting that there were kinetic differences between the individual mutant enzymes.

As a means of measuring the affinity of the mutant enzymes for the alkylating agent, the ability of mechlorethamine to inhibit a glutathione S-transferase-catalyzed reaction was assayed for each of the mutant enzymes. The results demonstrated that the affinities of the mutant enzymes for mechlorethamine did not differ strikingly from that of the wild-type enzyme, being slightly reduced in some instances. Thus the mechanism for the demonstrated increase in enzymatic activity cannot be assigned entirely to increased substrate binding. Nevertheless, the mutant isoforms of the enzymes clearly conferred a resistance level to mechlorethane which was increased over the capability of the wild type enzyme.

Note Regarding Sequence Listings

The numbering convention used in the specification above differs from the convention used in the SEQUENCE LISTING below, prepared in the format required by the Patent and Trademark Office. The applicant's convention does not number the first amino acid, the N-terminal methionine, while the SEQUENCE LISTING does number that amino acid. References in the specification to amino acid number must be adjusted by one when referring to the following sequence listings.

What is claimed is:

1. A method for creating a mutagenized glutathione-S-transferase enzyme having the ability to confer upon a host cell heightened resistance to a selected toxic electrophilic agent, comprising the steps of
   (a) creating a plurality of cultures of bacterial cells, the cultures having randomly created mutagenized isoforms of a glutathione S-transferase enzyme;
   (b) exposing the cultures to the electrophilic agent under conditions such that some of the cultures are killed while at least some cells in some of the cultures survive; and
   (c) recovering one or more genes encoding the mutagenized glutathione S-transferase enzyme isoforms from the cells which survive the exposure to the electrophilic agent.

2. The method as claimed in claim 1 wherein the step (a) includes creating site directed random mutations of the gene encoding the glutathione S-transferase at the sites of the codons encoding the amino acids forming the H-site of the enzyme.

3. The method as claimed in claim 1 wherein the selected electrophilic agent is an antineoplastic agent.

4. The method as claimed in claim 2 wherein the randomly mutagenized codons are at amino acid locations corresponding to amino acids number 10–12, 109–111, and 211 to 221 of SEQ ID NO: 2.

5. The method as claimed in claim 4 wherein the step of creating site directed random mutations includes constructing oligonucleotides for every possible coding pattern at at least one of the amino acid locations.

6. An artificial DNA construct for conferring upon a host cell enhanced resistance to an antineoplastic agent, the DNA construct comprising a protein coding sequence and flanking sequences effective to express the protein coding sequence in a host cell, the protein coding sequence coding for a non-native mutagenized isoform of glutathione S-transferase which, upon introduction into the host cell, confers upon the cell an enhanced level of resistance to the antineoplastic agent as compared to a comparable host cell not carrying the artificial DNA construct.

7. The DNA construct as claimed in claim 6 wherein the protein coding sequence further comprises, 5' to the sequence encoding the mutagenized glutathione-S-transferase, a sequence encoding a nuclear localization signal peptide directing active transport of glutathione S-transferase in the host cell into the nucleus of the cell.

8. A DNA construct as claimed in claim 6 further including at its 3' end a protein coding sequence encoding a membrane bound domain.

9. The DNA construct as claimed in claim 6 further comprising as a part of the flanking regulatory sequences an antioxidant responsive element which enhances the expression of the glutathione S-transferase in the presence of antioxidant molecules.

10. A DNA construct as claimed in claim 6 wherein the mutagenized isoform encoded by the protein coding sequence differs from native isoforms by at least one of the amino acid locations corresponding to amino acids 10–12, 109–111 and 211–221 in SEQ ID NO: 2.

11. A DNA construct comprising a protein coding region selected from the group consisting of the protein coding regions of SEQ ID NO: 3, 5, 7, 9, 11, 13, 15, 17 and 19.

* * * * *

UNITED STATES PATENT AND TRADEMARK OFFICE
CERTIFICATE OF CORRECTION

PATENT NO.    : 6,136,605
DATED         : October 24, 2000
INVENTOR(S)   : Fahl et al.

Page 1 of 1

It is certified that error appears in the above-identified patent and that said Letters Patent is hereby corrected as shown below:

<u>Title page,</u>
Item [75], Inventors, please remove "Ralph B. Puchalski, La Jolla, Calif.; Katharine Kramer; Wyeth W. Wasserman, both of Madison, Wis."

Signed and Sealed this

Twenty-fifth Day of March, 2003

JAMES E. ROGAN
*Director of the United States Patent and Trademark Office*